(12) United States Patent
Garimella et al.

(10) Patent No.: US 10,317,364 B2
(45) Date of Patent: Jun. 11, 2019

(54) METHOD AND APPARATUS FOR ION MOBILITY SEPARATIONS UTILIZING ALTERNATING CURRENT WAVEFORMS

(71) Applicant: Battelle Memorial Institute, Richland, WA (US)

(72) Inventors: Venkata B S Garimella, Richland, WA (US); Ahmed M. Hamid, Richland, WA (US); Yehia M. Ibrahim, West Richland, WA (US); Richard D. Smith, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 15/774,837

(22) PCT Filed: Aug. 15, 2016

(86) PCT No.: PCT/US2016/047070
§ 371 (c)(1),
(2) Date: May 9, 2018

(87) PCT Pub. No.: WO2017/062102
PCT Pub. Date: Apr. 13, 2017

(65) Prior Publication Data
US 2019/0004011 A1 Jan. 3, 2019

Related U.S. Application Data

(60) Provisional application No. 62/238,291, filed on Oct. 7, 2015.

(51) Int. Cl.
*G01N 27/62* (2006.01)
*H01J 49/06* (2006.01)
(Continued)

(52) U.S. Cl.
CPC ........ *G01N 27/624* (2013.01); *H01J 49/0027* (2013.01); *H01J 49/062* (2013.01); *H01J 49/26* (2013.01)

(58) Field of Classification Search
None
See application file for complete search history.

(56) References Cited

U.S. PATENT DOCUMENTS

| 4,777,363 A | 10/1988 | Eiceman et al. |
| 5,206,506 A | 4/1993 | Kirchner |

(Continued)

FOREIGN PATENT DOCUMENTS

| AU | 2014251354 B2 | 11/2017 |
| AU | 2016320584 A1 | 4/2018 |

(Continued)

OTHER PUBLICATIONS

Hamid, Ahmed M. et al., "Characterization of Travelling Wave Ion Mobility Separations in Structures for Lossless Ion Manipulations," *Analytical Chemistry*, 87(22):11301-11308 (Nov. 2015).

(Continued)

*Primary Examiner* — Andrew Smyth
(74) *Attorney, Agent, or Firm* — Klarquist Sparkman, LLP

(57) ABSTRACT

Methods and apparatuses for ion manipulations, including ion trapping, transfer, and mobility separations, using traveling waves (TW) formed by continuous alternating current (AC) are disclosed. An apparatus for ion manipulation includes a surface to which are coupled a first plurality of continuous electrodes and a second plurality of segmented electrodes. The second plurality of segmented electrodes is arranged in longitudinal sets between or adjacent to the first plurality of electrodes. An RF voltage applied to adjacent electrodes of the first plurality of electrodes is phase shifted (Continued)

by approximately 180° to confine ions within the apparatus. An AC voltage waveform applied to adjacent electrodes within a longitudinal set of the second plurality of segmented electrodes is phase shifted on the adjacent electrodes by 1°-359° to move ions longitudinally through the apparatus for separation.

24 Claims, 21 Drawing Sheets

(51) Int. Cl.
 H01J 49/00 (2006.01)
 H01J 49/26 (2006.01)

(56) References Cited

U.S. PATENT DOCUMENTS

| | | | |
|---|---|---|---|
| 5,572,035 A | 11/1996 | Franzen | |
| 5,834,771 A | 11/1998 | Yoon et al. | |
| 6,107,628 A | 8/2000 | Smith et al. | |
| 6,417,511 B1 | 7/2002 | Russ, IV | |
| 6,891,157 B2 | 5/2005 | Bateman et al. | |
| 6,960,760 B2 | 11/2005 | Bateman et al. | |
| 7,095,013 B2 | 8/2006 | Bateman et al. | |
| 7,151,255 B2 | 12/2006 | Weiss et al. | |
| 7,157,698 B2 | 1/2007 | Makarov et al. | |
| 7,180,078 B2 | 2/2007 | Pau et al. | |
| 7,365,317 B2 | 4/2008 | Whitehouse et al. | |
| 7,391,021 B2 | 6/2008 | Stoermer et al. | |
| 7,405,401 B2 | 7/2008 | Hoyes | |
| 7,548,818 B2 | 6/2009 | Kieser | |
| 7,786,435 B2 | 8/2010 | Whitehouse et al. | |
| 7,838,826 B1 | 11/2010 | Park | |
| 7,872,228 B1 | 1/2011 | Kim et al. | |
| 7,888,635 B2 | 2/2011 | Belov et al. | |
| 7,928,375 B1 | 4/2011 | Mangan et al. | |
| 8,003,934 B2 | 8/2011 | Hieke | |
| 8,049,169 B2 | 11/2011 | Satake et al. | |
| 8,222,597 B2 | 7/2012 | Kim et al. | |
| 8,319,180 B2 | 11/2012 | Nikolaev et al. | |
| 8,373,120 B2 | 2/2013 | Verentchikov | |
| 8,389,933 B2 | 3/2013 | Hoyes | |
| 8,410,429 B2 | 4/2013 | Franzen et al. | |
| 8,581,181 B2 | 11/2013 | Giles | |
| 8,809,769 B2 | 8/2014 | Park | |
| 8,835,839 B1* | 9/2014 | Anderson | H01J 49/06 250/290 |
| 8,901,490 B1 | 12/2014 | Chen et al. | |
| 8,907,273 B1 | 12/2014 | Chen et al. | |
| 8,969,800 B1 | 3/2015 | Tolmachev et al. | |
| 9,704,701 B2 | 7/2017 | Ibrahim et al. | |
| 9,812,311 B2 | 11/2017 | Anderson et al. | |
| 9,966,244 B2 | 5/2018 | Anderson et al. | |
| 2001/0035498 A1 | 11/2001 | Li | |
| 2003/0132379 A1 | 7/2003 | Li | |
| 2004/0026611 A1 | 2/2004 | Bateman et al. | |
| 2004/0089803 A1 | 5/2004 | Foley | |
| 2004/0222369 A1 | 11/2004 | Makarov et al. | |
| 2005/0040327 A1 | 2/2005 | Lee et al. | |
| 2005/0109930 A1 | 5/2005 | Hill, Jr. et al. | |
| 2007/0138384 A1 | 6/2007 | Keiser | |
| 2009/0173880 A1 | 7/2009 | Bateman et al. | |
| 2009/0206250 A1 | 8/2009 | Wollnik | |
| 2011/0049357 A1* | 3/2011 | Giles | H01J 49/062 250/283 |
| 2011/0192969 A1 | 8/2011 | Verentchikov | |
| 2014/0061457 A1 | 3/2014 | Berdnikov et al. | |
| 2014/0124663 A1 | 5/2014 | Green et al. | |
| 2014/0145076 A1 | 5/2014 | Park | |
| 2014/0299766 A1 | 10/2014 | Anderson et al. | |
| 2015/0028200 A1 | 1/2015 | Green et al. | |
| 2015/0364309 A1 | 12/2015 | Welkie | |
| 2016/0027604 A1 | 1/2016 | Cho et al. | |
| 2016/0049287 A1 | 2/2016 | Ding et al. | |
| 2016/0071715 A1 | 3/2016 | Anderson et al. | |
| 2017/0076931 A1 | 3/2017 | Ibrahim et al. | |
| 2017/0125229 A1 | 5/2017 | Giles et al. | |
| 2018/0061621 A1 | 3/2018 | Anderson et al. | |
| 2018/0254178 A1 | 9/2018 | Ibrahim et al. | |

FOREIGN PATENT DOCUMENTS

| | | |
|---|---|---|
| AU | 2016335524 A9 | 5/2018 |
| CA | 2908936 | 10/2014 |
| CA | 2997910 | 3/2017 |
| CA | 3000341 | 4/2017 |
| CN | 1361922 | 7/2002 |
| CN | 101126738 | 2/2008 |
| CN | 102163531 | 8/2011 |
| CN | 102945786 | 2/2013 |
| CN | 201680069722 | 8/2016 |
| CN | 105264637 B | 9/2017 |
| CN | 107507751 A | 12/2017 |
| CN | 108352288 A | 7/2018 |
| DE | 112013004733 | 6/2015 |
| EP | 1566828 | 8/2005 |
| EP | 1825495 | 8/2007 |
| EP | 2065917 | 6/2009 |
| EP | 2913839 | 9/2015 |
| EP | 2984675 A1 | 2/2016 |
| EP | 3347913 A1 | 7/2018 |
| EP | 3359960 A1 | 8/2018 |
| GB | 2440970 | 2/2008 |
| GB | 2506362 | 4/2014 |
| JP | 2002015699 | 1/2002 |
| JP | 2009532822 | 9/2009 |
| JP | 2009535759 | 10/2009 |
| JP | 2009537070 | 10/2009 |
| JP | 2011529623 | 12/2011 |
| JP | 2012503286 | 2/2012 |
| JP | 2016514896 A | 5/2016 |
| JP | 2018-518405 | 8/2016 |
| JP | 2018528427 A | 9/2018 |
| SG | 11201801852 | 5/2016 |
| SG | 11201802494 | 8/2016 |
| SG | 11201508277 | 2/2018 |
| WO | WO 2006/064274 | 6/2006 |
| WO | WO 2007/133469 | 11/2007 |
| WO | WO 2010/014077 | 2/2010 |
| WO | WO 2010/032015 | 3/2010 |
| WO | WO 2011/089419 | 7/2011 |
| WO | WO 2012/116765 | 9/2012 |
| WO | WO 2013/018529 | 2/2013 |
| WO | WO 2014/048837 | 4/2014 |
| WO | WO 2014/168660 | 10/2014 |
| WO | WO 2015/056872 | 4/2015 |
| WO | WO2015/097462 | 7/2015 |
| WO | WO 2016/069104 | 5/2016 |
| WO | WO 2017/044159 | 3/2017 |
| WO | WO 2017/062102 | 4/2017 |

OTHER PUBLICATIONS

International Search Report and Written Opinion for PCT/US2016/047070 (dated Nov. 7, 2016).
Tolmachev, Aleksey V. et al., "Characterization of Ion Dynamics in Structures for Lossless Ion Manipulations," *Analytical Chemistry*, 86(18):9162-9168 (Sep. 2014).
Chen, et al., "Mobility-Selected Ion Trapping and Enrichment Using Structures for Lossless Ion Manipulations", Analytical Chemistry, Jan. 2016, 88, pp. 1728-1733.
Deng et al., "Serpentine Ultralong Path with Extended Routing (SUPER) High Resolution Traveling Wave Ion Mobility-MS using Structures for Lossles Ion Manipulations", Analytical Chemistry, Mar. 2017, 89, pp. 4628-4634.
International Search Report and Written Opinion for related International Application No. PCT/US2018/041607, dated Sep. 20, 2018, 18 pp.
Webb et al., "Mobility-Resolved Ion Selection in Uniform Drift Field Ion Mobility Spectrometry/Mass Spectrometry: Dynamic Switch-

(56) References Cited

OTHER PUBLICATIONS ing in Structures for Lossless Ion Manipulations," Analytical Chemistry, Oct. 2014, 86, 9632-9637.
Wojcik et al., "Lipid and Glycolipid Isomer Analyses Using Uitra-High Resolution Ion Mobility Spectrometry Separations", International Jouranl of Molecular Sciences, Jan. 2017, 18, 12 pp.
Examination Report No. 2 for related Australian Applicatian No. 2016320584, dated Sep. 3, 2018, 2 pages.
Examination Report No. 1 for related Australian Application No. 2016335524, dated May 15, 2018, 4 pages.
First Office Action for related Canadian Application No. 3,000,341, dated Jul. 30, 2018, 5 pages.
First Office Action for Chinese Application No. 201680065673.2, dated Sep. 30, 2018, 6 pages (English translation not yet available).
Written Opinion from the Intellectual Property Office of Singapore for related Application No. 11201802494Q, dated Aug. 21, 2018, 8 pages.
Written Opinion from the Intellectual Property Office of Singapore for related Application No. 11201801852Q, dated Nov. 22, 2018, 9 pages.
International Search Report and Written Opinion for related International Application No. PCT/US2018/046752, dated Dec. 4, 2018, 12 pp.
First Office Action for related Japanese Application No. 2018-513012, dated Aug. 2, 2018, 2 pages; with English translation, 2 pages.
First Office Action for related Chinese Application No. 201680065673.2, dated Sep. 30, 2018, 6 pages.
English translation of the first Chinese office action from corresponding Chinese patent application No. 201480032436.7, dated Oct. 14, 2016, 5 pages.
English translation of the search report from corresponding Chinese patent application No. 201480032436.7, dated Sep. 29, 2016, 2 pages.
European Search Report for European Patent Application No. 14782685.3, dated Oct. 25, 2016.
Examination Report No. 1 for related Australian Application No. 2016320584, dated Jun. 27, 2018, 3 pages.
First Office Action for related Canadian Application No. 2,997,910, dated May 4, 2018, 4 pages.
International Search Report and Written Opinion issued in related International Application No. PCT/US2016/030455, dated Jul. 25, 2016, 19 pages.
International Search Report and Written Opinion for related International Application No. PCT/US2014/011291, dated Jun. 6, 2014, 2 pages.
Search Report from corresponding Singapore patent application No. 11201508277X, dated Mar. 6, 2016, 7 pages.

* cited by examiner

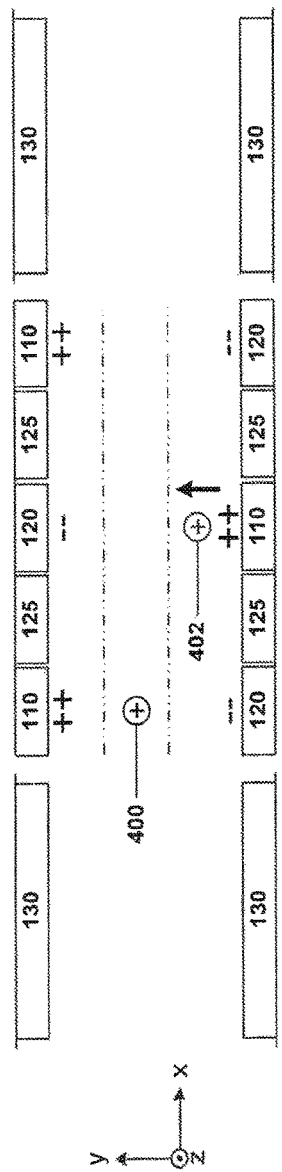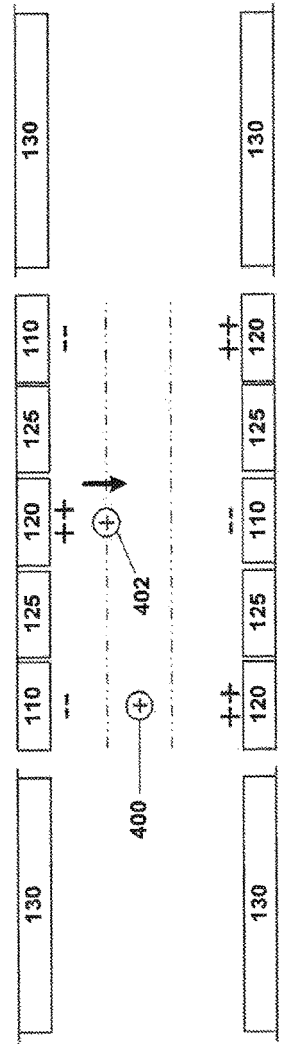
FIG. 4A
FIG. 4B

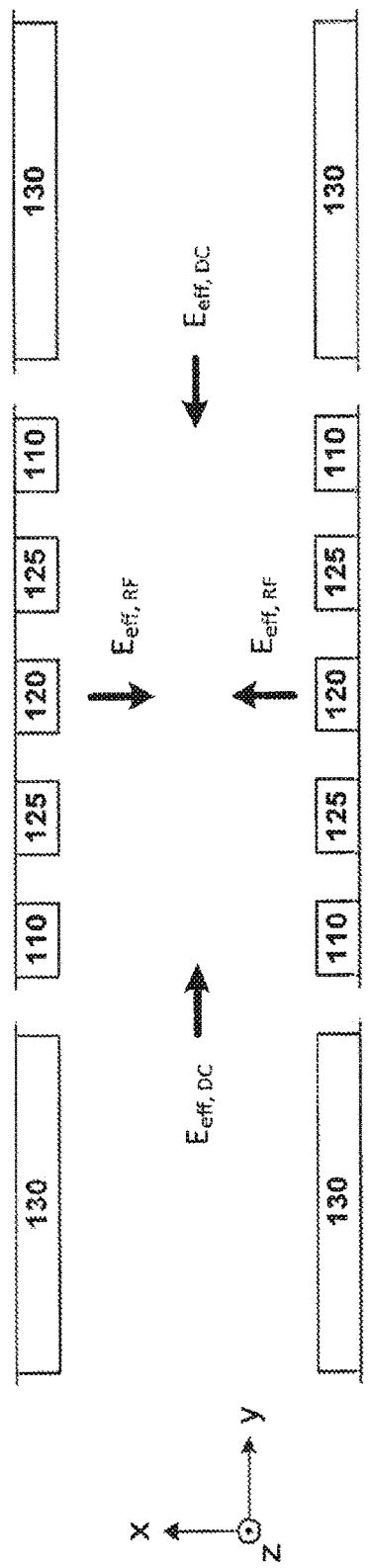

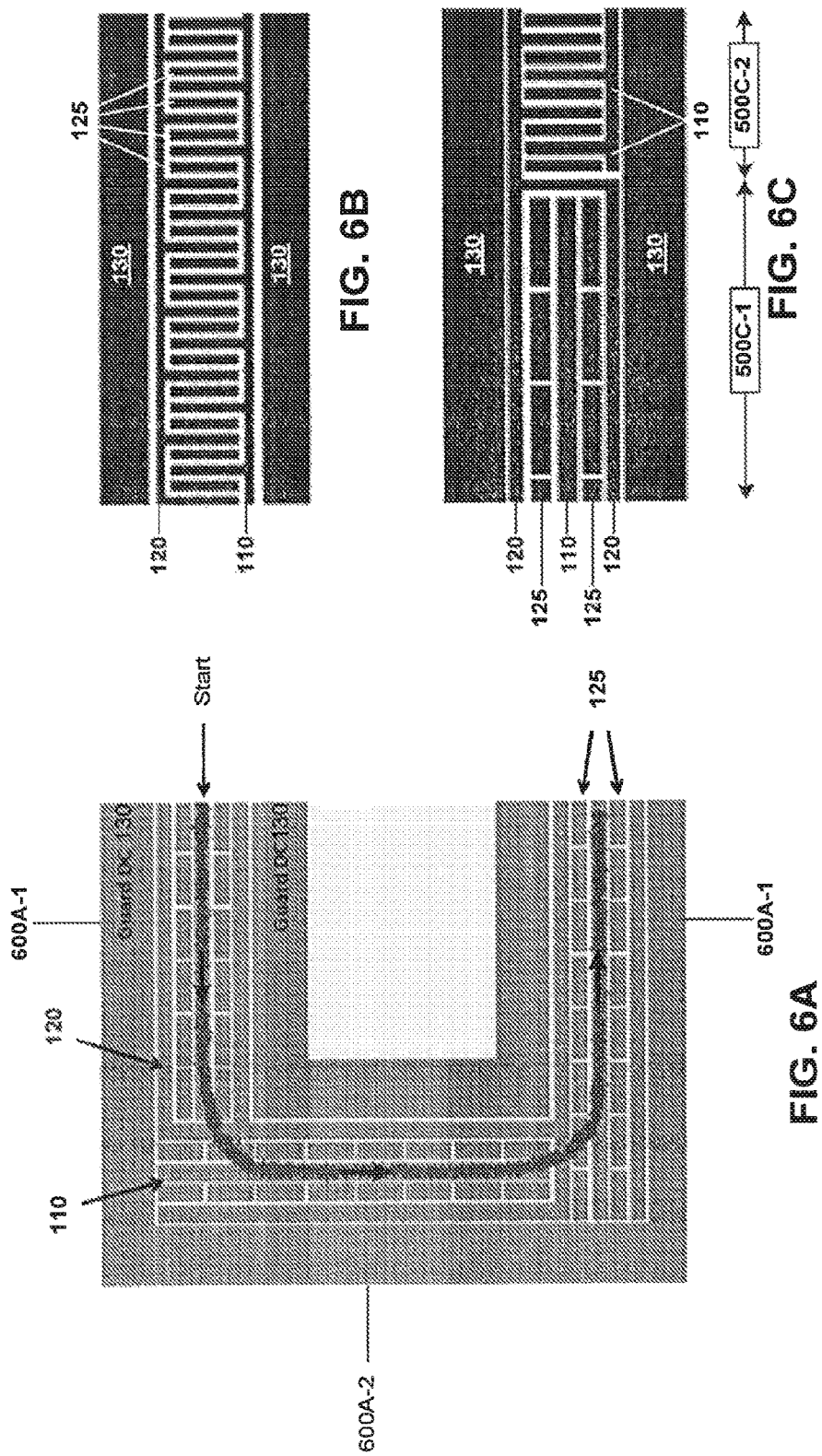

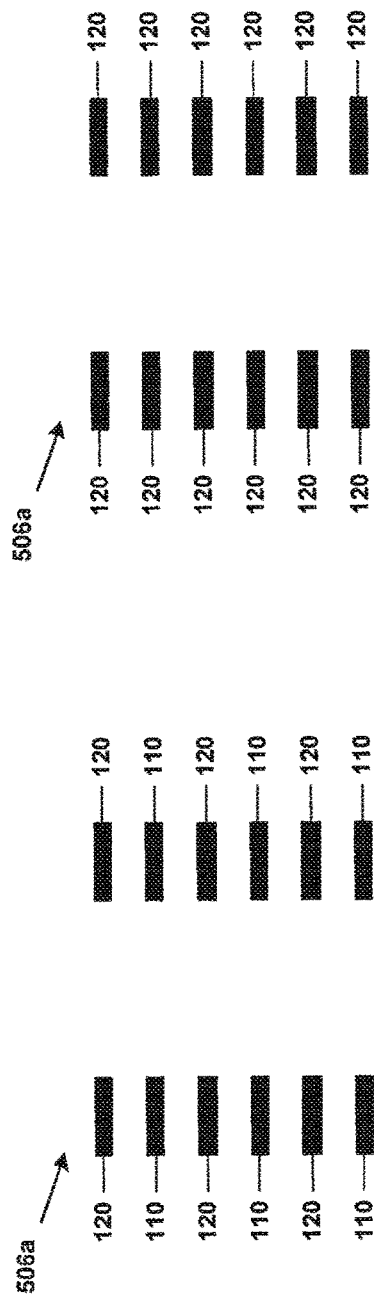

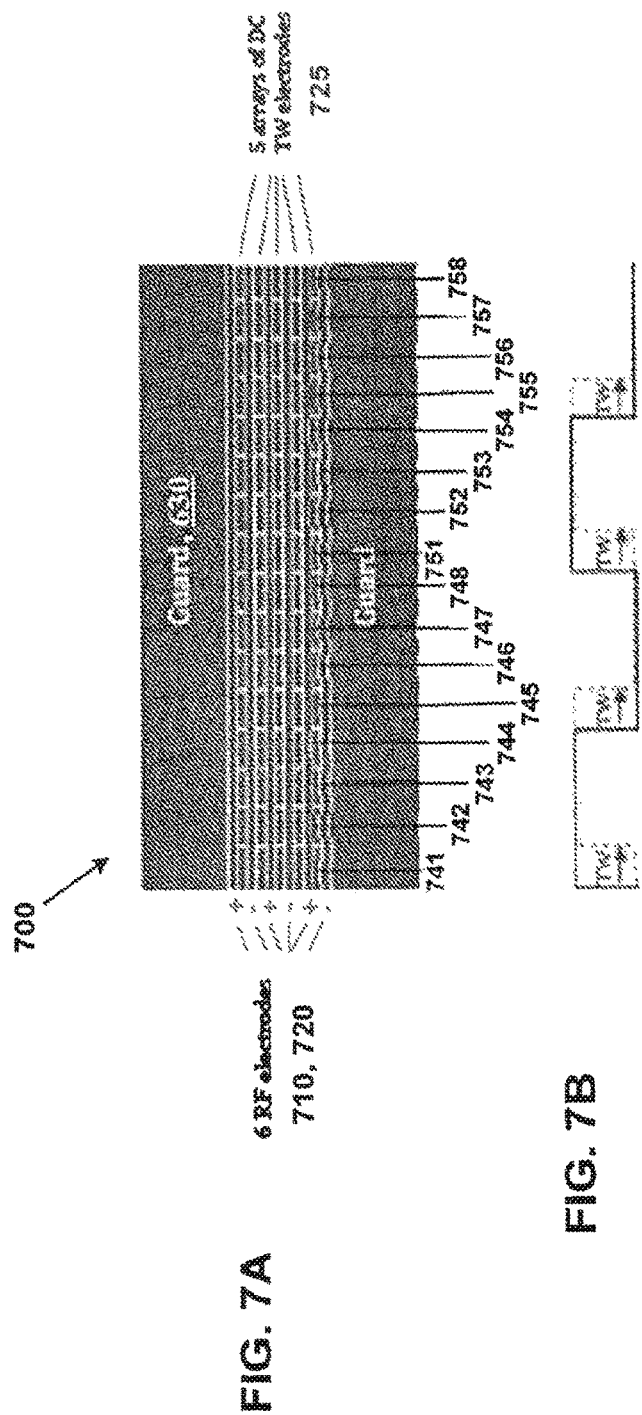

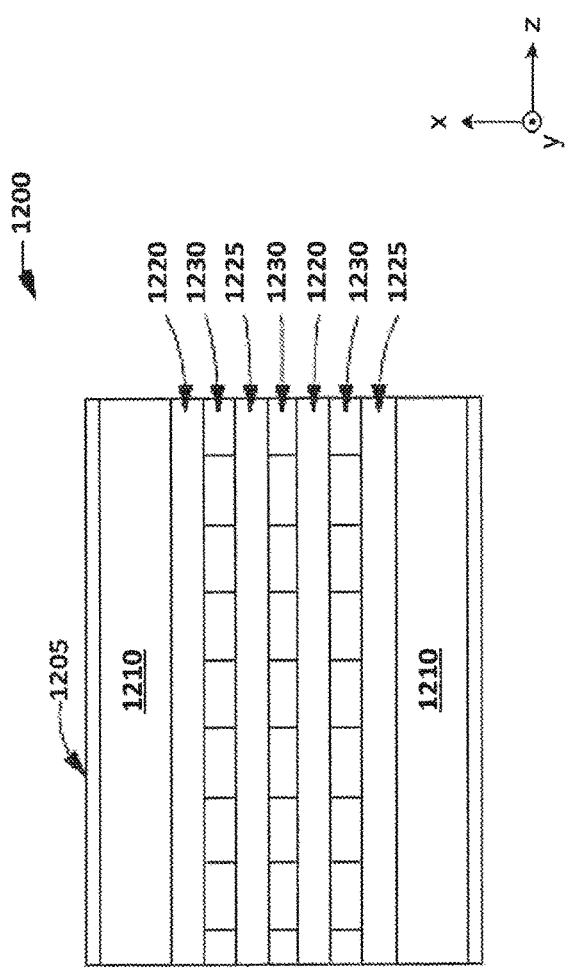

METHOD AND APPARATUS FOR ION MOBILITY SEPARATIONS UTILIZING ALTERNATING CURRENT WAVEFORMS

CROSS-REFERENCE TO RELATED APPLICATIONS

This is the U.S. National Stage of International Application No. PCT/US2016/047070, filed Aug. 15, 2016, which was published in English under PCT Article 21(2), which in turn claims the benefit of U.S. Provisional Application Ser. No. 62/238,291, filed Oct. 7, 2015, titled "METHOD AND APPARATUS FOR CONTROLLING IONS IN A GAS PHASE," all of which are hereby incorporated by reference in their entirety for all of its teachings.

STATEMENT REGARDING FEDERALLY SPONSORED RESEARCH OR DEVELOPMENT

This invention was made with Government support under Contract DE-AC0576RLO1830 awarded by the U.S. Department of Energy and Grant No. GM103493 awarded by the National Institutes of Health. The Government has certain rights in the invention.

TECHNICAL FIELD

Embodiments of the present disclosure relate to ion mobility separations and related ion manipulations. More specifically, the disclosed embodiments relate to performing ion manipulations including movement in moving ion trapping regions and ion mobility separations using a continuous, alternating current (AC) voltage waveform or, multiple continuous AC voltage waveforms, applied to one or more segmented electrodes.

BACKGROUND

Ion mobility spectrometry (IMS) is a technique for separating and identifying ions. IMS can be employed to separate structural isomers and resolve conformational features of macromolecules. IMS may also be employed to augment mass spectroscopy (MS) in a broad range of applications, including metabolomics, glycomics, and proteomics.

For example, when performing IMS, a sample containing different ions is injected into a first end of an enclosed cell containing a carrier gas, also referred to as a buffer gas. In the cell, the ions move from the first end of the cell to a second end of the cell under the influence of an applied electric field. The ions are subsequently detected at the second end of the cell as a current as a function of time. The sample ions achieve a maximum, constant velocity (i.e., a terminal velocity) arising from the net effects of acceleration due to the applied electric field and deceleration due to collisions with the buffer gas molecules. The terminal velocity of ion within the IMS cell is proportional to their respective mobilies, related to ion characteristics such as mass, size, shape, and charge. Ions that differ in one or more of these characteristics will exhibit different mobilities when moving through a given buffer gas under a given electric field and, therefore, different terminal velocities. As a result, each ion exhibits a characteristic time for travel from the first end of the cell to the second end of the cell. By measuring this characteristic travel time for ions within a sample, the ions may be identified.

There are a number of IMS formats used for chemical and biochemical analysis, including constant field drift tube ion mobility spectrometry (DT-IMS), high field asymmetric ion mobility spectrometry (FA-IMS), differential mobility analysis (DMA), and traveling wave ion mobility spectrometry (TW-IMS). These formats vary in the manner by which the electric field is applied to separate the ions within the IMS cell. Notably, however, conventional IMS devices are limited in their ability to separate ions (separation power) due to practical limitations on size and complexity of the electrode structures generating the electric fields that separate the ions.

Accordingly, there exists an ongoing need for improved systems and methods for ion mobility separation.

SUMMARY

In an embodiment of the disclosure, an apparatus for ion manipulations is provided. The apparatus includes at least one surface, a first plurality of continuous electrodes, and a second plurality of segmented electrodes. The first plurality of continuous electrodes is coupled to the at least one surface and in electrical communication with a radiofrequency (RF) voltage source. An RF voltage applied to adjacent electrodes of the first plurality of electrodes by the RF voltage source is phase shifted on the adjacent electrodes of the first plurality of electrodes by approximately 180°. The second plurality of segmented electrodes is coupled to the at least one surface and arranged in longitudinal sets between or adjacent to the first plurality of electrodes. The second plurality of segmented electrodes is further in electrical communication with an alternating current (AC) voltage source. An AC voltage waveform applied to adjacent electrodes within a longitudinal set of the second plurality of segmented electrodes by the AC voltage source is phase shifted on the adjacent electrodes of the second plurality of electrodes by 1°-359°.

Embodiments of the apparatus may include one or more of the following, in any combination.

In an embodiment, the apparatus further includes a plurality of guard electrodes positioned on outer ends of the first and second plurality of electrodes on the at least one surface. The plurality of guard electrodes are in electrical communication with a DC voltage source. The plurality of guard electrodes generate electric fields that constrain ion motion towards the guard electrodes when receiving a constant DC voltage from the DC voltage source.

In an embodiment of the apparatus, the AC voltage waveform is a sine wave.

In an embodiment of the apparatus, the AC voltage waveform is the sum of more than one AC voltage waveform.

In an embodiment of the apparatus, the AC voltage waveform applied to adjacent electrodes within a longitudinal set of the second plurality of segmented electrodes is phase shifted on the adjacent electrodes of the second plurality of segmented electrodes in a repeating pattern.

In an embodiment of the apparatus, the AC voltage waveform applied to adjacent electrodes within a longitudinal set of the second plurality of segmented electrodes is phase shifted by approximately 45°, 90° or 120° on the adjacent electrodes of the second plurality of electrodes in a stepwise fashion.

In an embodiment of the apparatus, the at least one surface includes a single and non-planar surface.

In an embodiment of the apparatus, the single, non-planar surface is one of the following shapes: curved, cylindrical, a spiral, a funnel, hemispherical, or elliptical.

In an embodiment of the apparatus, the at least one surface includes two surfaces spaced apart from one another.

In an embodiment of the apparatus, the two surfaces are approximately parallel to one another.

In an embodiment of the apparatus, a frequency of the applied AC voltage waveform is selected from the range of 10 Hz-200 kHz, and a frequency of the applied RF voltage is selected from the range of 100 kHz-5 MHz.

In an embodiment of the apparatus, a frequency applied AC voltage waveform is selected from the range of 1 Hz to 1 kHz.

In an embodiment of the apparatus, a pressure range of the apparatus is from atmospheric pressure to 1 mtorr vacuum.

In another embodiment of the disclosure, an apparatus for ion manipulations is provided. The apparatus includes at least one surface and a plurality of segmented electrodes. The plurality of segmented electrodes is coupled to the at least one surface and arranged in one or more longitudinal sets. The plurality of segmented electrodes is further in electrical communication with an alternating current (AC) voltage source and a radiofrequency (RF) voltage source. An AC voltage waveform applied to adjacent electrodes within a longitudinal set of the plurality of electrodes by the AC voltage source is phase shifted by 1°-359°. An RF voltage applied to adjacent electrodes of the plurality of electrodes by the RF voltage source is phase shifted by approximately 180°.

Embodiments of the apparatus may include one or more of the following in any combination.

In an embodiment, the apparatus further includes a plurality of guard electrodes positioned on outer ends of the plurality of electrodes on the at least one surface. The plurality of guard electrodes are further in electrical communication with a DC voltage source. The plurality of guard electrodes generate electric fields that constrain ion motion towards the plurality of guard electrodes when receiving a constant DC voltage from the DC voltage source.

In an embodiment of the apparatus, the applied AC voltage waveform is a sine wave.

In an embodiment of the apparatus, the AC voltage waveform is the sum of more than one AC voltage waveform.

In an embodiment of the apparatus, the applied the AC voltage waveform is phase shifted on the adjacent electrodes of the plurality of electrodes in a repeating pattern.

In an embodiment of the apparatus, the applied AC voltage waveform is phase shifted by approximately 45°, 90°, 120°, or 180° on the adjacent electrodes of the plurality of electrodes in a stepwise fashion.

In an embodiment of the apparatus, the at least one surface includes a single and non-planar surface.

In an embodiment of the apparatus, the single, non-planar surface is one of the following shapes: curved, cylindrical, a spiral, a funnel, hemispherical, or elliptical.

In an embodiment of the apparatus, the at least one surface includes two surfaces spaced apart from one another.

In an embodiment of the apparatus, the two surfaces are approximately parallel to one another.

In an embodiment of the apparatus, a frequency of the applied AC voltage waveform is selected from the range of 1 kHz-200 kHz, and the RF voltage is selected from the range of 100 kHz-5 MHz.

In an embodiment of the apparatus, a pressure range of the apparatus is from atmospheric pressure to 1 mtorr vacuum.

In an additional embodiment of the disclosure, a method of ion manipulations is provided. The method includes providing at least one surface. The at least one surface includes a first plurality of continuous electrodes coupled to the at least one surface and in electrical communication with a radiofrequency (RF) voltage source. The at least one surface further includes a second plurality of segmented electrodes coupled to the at least one surface and arranged in longitudinal sets between or adjacent to the first plurality of electrodes. The second plurality of segmented electrodes is further in electrical communication with an alternating current (AC) voltage source. The method further includes applying, by the RF voltage source, an RF voltage to adjacent electrodes of the first plurality of electrodes, where the applied RF voltage is phase shifted on the adjacent electrodes of the first plurality of electrodes by approximately 180°. The method additional includes applying, by the AC voltage source, an AC voltage waveform within a longitudinal set of the second plurality of segmented electrodes, where the applied AC voltage waveform is phase shifted on the adjacent electrodes of the second plurality of electrodes by 1°-359°.

Embodiments of the method may include one or more of the following, in any combination.

In an embodiment, the method further includes positioning a plurality of guard electrodes on outer ends of the first and second plurality of electrodes on the at least one surface. The plurality of guard electrodes are further in electrical communication with a DC voltage source. The plurality of guard electrodes generate electric fields that constrain ion motion towards the guard electrodes when receiving a constant DC voltage from the DC voltage source.

In an embodiment of the method, the AC voltage waveform is a sine wave.

In an embodiment of the method, the AC voltage waveform is the sum of more than one AC voltage waveform.

In an embodiment of the method, the applied AC voltage waveform is phase shifted on the adjacent electrodes of the second plurality of segmented electrodes in a repeating pattern.

In an embodiment of the method, the applied AC voltage waveform is phase shifted by approximately 45°, 90°, or 120° on the adjacent electrodes of the second plurality of segmented electrodes in a stepwise fashion.

In an embodiment of the method, the at least one surface includes a single and non-planar surface.

In an embodiment of the method, the single, non-planar surface is one of the following shapes: curved, cylindrical, a spiral, a funnel, hemispherical, or elliptical.

In an embodiment of the method, the at least one surface includes two surfaces spaced apart from one another.

In an embodiment of the method, the two surfaces are approximately parallel to one another.

In an embodiment of the method, a frequency of the applied AC voltage waveform is selected from the range of 10 Hz-200 kHz, and a frequency of the RF voltage is selected from the range of 100 kHz-5 MHz.

In another embodiments of the disclosure, a method of ion manipulation is provided. The method includes providing at least one surface including a plurality of segmented electrodes coupled to the at least one surface and arranged in one or more longitudinal sets. The plurality of segmented electrodes are in electrical communication with an alternating current (AC) voltage source and a radiofrequency (RF) voltage source. The method further includes applying, by the AC voltage source, an AC voltage waveform to adjacent electrodes within a set of the plurality of segmented electrodes. The applied AC voltage waveform is phase shifted on the adjacent electrodes of the plurality of segmented electrodes by 1°-359°. The method also includes applying, by the RF voltage source, an RF voltage to adjacent electrodes of the plurality of segmented electrodes. The applied RF voltage is phase shifted on the adjacent electrodes of the plurality of segmented electrodes by approximately 180°.

Embodiments of the method may include one or more of the following, in any combination.

In an embodiment, the method further includes positioning a plurality of guard electrodes on outer ends of the plurality of segmented electrodes on the at least one surface. The plurality of guard electrodes is further in electrical communication with a DC voltage source. The plurality of guard electrodes generate electric fields that constrain ion motion towards the guard electrodes when receiving a constant DC voltage from the DC voltage source.

In an embodiment of the method, the AC voltage waveform is a sine wave.

In an embodiment of the method, the AC voltage waveform is the sum of more than one AC voltage waveform wave.

In an embodiment of the method, the applied AC voltage waveform is shifted on the adjacent electrodes of the plurality of segmented electrodes in phase in a repeating pattern.

In an embodiment of the method, the applied AC voltage waveform is phase shifted on the adjacent electrodes of the plurality of segmented electrodes by approximately 45°, 90°, or 120° in a stepwise fashion.

In an embodiment of the method, the at least one surface includes a single and non-planar surface.

In an embodiment of the method, the single, non-planar surface is one of the following shapes: curved, cylindrical, a spiral, a funnel, hemispherical, or elliptical.

In an embodiment of the method, the at least one surface includes two surfaces spaced apart from one another.

In an embodiment of the method, the two surfaces are approximately parallel to one another.

In an embodiment of the method, a frequency of the applied AC voltage waveform is selected from the range of 10 Hz-200 kHz, and a frequency of the applied RF voltage is selected within the range of 100 kHz-5 MHz.

In an embodiment, the electrodes may be arranged to cause ions to be trapped and accumulated in a region of an ion manipulation device, such as, but not limited to, the device described in U.S. Pat. No. 8,835,839, incorporated by reference in its entirety.

In an embodiment, the AC waveform can be adjusted to change, reduce, or eliminate a degree of ion heating by the AC traveling waveform compared to the transient application of DC voltages.

In an embodiment, the ion mobility separation can be stopped by increasing the amplitude of the AC waveform.

In one embodiment, the AC traveling waveform is stopped by changing the phase shift applied to adjacent AC electrodes to approximately zero or by reducing the AC frequency to approximately zero.

BRIEF DESCRIPTION OF THE DRAWINGS

FIGS. 4A-4B are schematic diagrams illustrating ion motion under the influence of electric fields generated by a first plurality of RF electrodes for confinement of the ions.

FIG. 4C is a schematic diagram illustrating net electric fields generated by the first plurality of RF electrodes and a plurality of guard electrodes for confinement of ions.

FIGS. 6A-6F are schematic illustrations of alternative embodiments of electrode configurations.

FIGS. 6G-6P are schematic illustrations of alternative embodiments of apparatus, including multiple levels, for performing ion separation using continuous AC waveforms.

FIG. 7A is a schematic illustration of an apparatus for performing ion separation employing transient DC voltages.

FIG. 7B is a schematic illustration of a transient DC voltage employed in conjunction with the apparatus of FIG. 7A.

FIG. 12 is a schematic illustration of an apparatus having a curved surface for performing ion separation employing transient DC voltages.

DETAILED DESCRIPTION

Figure 1:
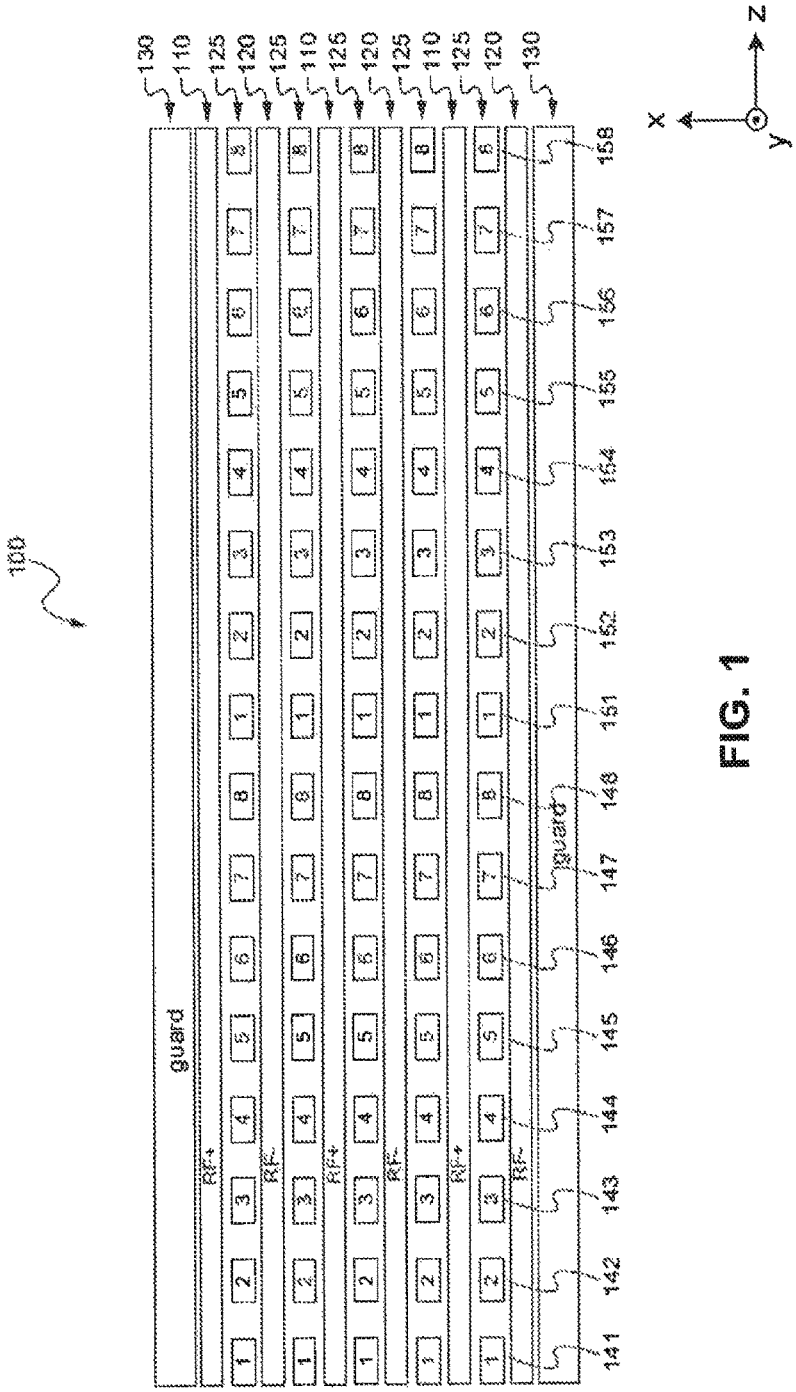
FIG. 1 is a schematic diagram of an apparatus for ion mobility separations, in accordance with a first embodiment of the present disclosure.

The following description includes embodiments of the present disclosure. These embodiments are not limited to these illustrated but also include a variety of modifications and embodiments thereto. Therefore, the present description should be seen as illustrative and not limiting. While the disclosed embodiments are susceptible of various modifications and alternative constructions, it should be understood, that there is no intention to limit the disclosure to the specific form discussed, but, on the contrary, the disclosure is to cover all modifications, alternative constructions, and equivalents falling within the spirit and scope of the disclosure as defined in the claims.

Embodiments of the present disclosure are directed to improved methods and apparatuses for separation of gas phase ions based on their mobilities employing continuous, alternating current (AC) waveforms or multiple continuous AC waveforms applied to one or more segmented electrodes. As discussed in detail below, these embodiments provide advantages over conventional ion mobility separation devices and methods, including reduced heating of ions, while providing comparable separation ability.

Conventional drift tube ion mobility separation (DT-IMS) employs a fixed voltage drop over the length of an IMS tube to provide a relatively weak, constant electric field under which ions move through the IMS tube. In this technique, ions are separated according to their relative mobilities when moving through a given buffer gas under a the applied electric field. The mobility is related to the collision cross-section of the ion with the inert buffer gas, the area around the ion in which the center of a buffer gas molecule must strike in order for a collision to occur. As discussed above, the collision cross-section is related to ion characteristics such as mass, size shape, and charge. In general, ions with a relatively larger collision cross-section possess lower mobility and vice versa. For example, an ion having a relatively low ion mobility (larger ion collision cross-section) will arrive at the detector at a later time as compared to an ion having a relatively larger ion mobility (smaller collision cross-section). Thus, by measuring the number of ion counts as a function of time, a spectrum of peaks and valleys is obtained. Comparing such spectra to spectra of known ions under the measurement conditions permits identification of the respective ions within a sample.

For any IMS measurements, it is desirable to adequately separate different ions so that they appear as distinct peaks IMS spectrum. That is to say, interpretation of IMS spectra becomes considerably more difficult when peaks due to different ions overlap. Thus, the ability of an IMS instrument to resolve closely spaced peaks is of significant interest.

In the context of conventional DT-IMS, increasing the resolving power, a quantity characterizing the separation efficiency of the IMS, requires increasing the magnitude of the voltage drop (V) over the length (d) of the tube. As discussed above, in DT-IMS, the electric field (E) is held constant and given by $E=V/d$. Accordingly, it may be understood that increasing the resolving power (increasing V) requires an increase in the length of the drift tube, d, to maintain a constant electric field. Therefore practical constraints on the magnitude of the voltage drop and the tube length, amongst other considerations, limit the resolving power achieved in DT-IMS.

Turning to another conventional IMS technique, traveling wave ion mobility separation (TW-IMS), a traveling electric field waveform is employed to move ions through the IMS tube, in contrast to the constant electric field discussed above. The traveling waveform in this case is generated by application of a transient and repetitive direct current (DC) voltage profile on a series of electrodes along the length of the IMS tube. For example, as discussed in greater detail below with respect to the example of FIG. 7, a transient DC voltage may be applied to the set of electrodes to form a square-like voltage profile across the set of electrodes. For example, a high and constant voltage is applied to a first subset of the electrodes and a low (e.g. zero) voltage applied to an immediately subsequent second subset of the electrodes. The DC voltage waveform is then time-stepped through the entire set of electrodes in steps such that an electrode receiving a high voltage at a first time step receives a low voltage at the next time step. This time-stepping is then propagated throughout the device to create the TW, typically with simple sequences of steps repeated many times over many electrodes in the device. The application of transient DC voltages (e.g., traveling waves) can eliminate the need for increasingly high voltages as the drift length increases.

In general, the variables affecting ion motion in TW-IMS are the amplitude of the traveling wave, the traveling wave velocity, and the operating pressure. The ability of an ion to keep up with the traveling wave in the presence of collisions with the buffer gas is a function of the ion's velocity (mobility). Depending on the ratio of the maximum ion velocity to the speed of the traveling wave, c, three modes of ion behavior are observed.

$c \gg 1$: When the maximum ion velocity is much greater than the speed of the traveling wave, $c \gg 1$, ions move through the device in effective and distinct ion trapping regions created by the TW. Thus, under this condition, ions move through and exit the device unseparated.

$c \ll 1$: When the maximum ion velocity is much less than the speed of the wave, $c \ll 1$, the ions have insufficient mobility to keep up with the TW. Under this circumstance, ions are largely unaffected by the TW. As a result, the ions become trapped inside the IMS device, not exiting the IMS device, or only slowing moving and exiting the IMS device, often with significant diffusional broadening.

$c \approx 1$: When the maximum ion velocity is approximately equal to the speed of the wave, $c \approx 1$, ions can move with the wave much of the time, but are also occasionally passed over by waves. Ions of lower velocity or mobility tend to fall behind more often than those of higher velocity or mobility, and ion separation is achieved.

Notably, however, commercially available TW-IMS devices have limited separation ability due to practical limitations on the size and complexity of the electrode structures. This limited separation ability can be inadequate for many potential applications, a challenge that is general to IMS, particularly where high sensitivity is also desired. Furthermore, because the transient DC voltages in conventional TW-IMS are applied in an on-or-off basis, the magnitude of the resultant electric field at the front of the wave is relatively high, as compared to the magnitude of the electric field used in DT-IMS. The high electric field in TW-IMS leads to ions spending more time in high electric fields and further results in some increased extent of internal 'heating' of ions compared to drift tube arrangements. This heating can lead to undesired changes of conformation or shape of ions, as well as reduced precision in the determination of collision cross-sections for ions being separated.

To address these limitations, embodiments of the disclosure present development and characterization of a new traveling wave-based Structure for Lossless Ion Manipulations (SLIMS) for ion mobility separations that employs continuous, alternating current (AC) voltage waveforms (AC-SLIMS) to form the traveling wave, as opposed to the transient DC voltage waveforms of conventional TW-IMS.

As discussed in greater detail below, certain embodiments of the AC-SLIMS apparatus include a first plurality of continuous radiofrequency (RF) electrodes and a second plurality of segmented AC electrodes. The first plurality of RF electrodes are mounted to a surface and positioned generally parallel to one another. The second plurality of segmented AC electrodes are positioned laterally adjacent to the first plurality of RF electrodes (e.g., interposed between). Application of RF voltages to the first plurality of continuous electrodes generates electric fields that provide ion confinement. Application of a continuous, time-varying AC voltage to the second plurality of segmented electrodes forms an alternating current (AC) voltage waveform to create a TW that generates an electric field to provide longitudinal ion motion and separation. The AC voltage waveform may be applied in the form of a sine wave, a cosine wave, or a combinations of multiple sine and/or cosine waves.

As illustrated below in the Examples, the AC-SLIMS approach achieves comparable resolution to conventional TW-IMS. Furthermore, an unexpected feature of the AC-SLIMS embodiments is that ions appear to spend less time at higher electric fields. As a result, ions separated using the AC-SLIMS approach undergo fewer conformational changes from ion heating, as compared to conventional TW-IMS using transient application of DC voltage waveforms. Furthermore since conformation changes also change the ion collision cross-section, reducing the number of these changes using the AC-SLIMS approach enables more precise measurement of ion collision cross-sections.

The ability of the AC-SLIMS approach to provide more precise measurement of collision cross-section is highly beneficial. In one aspect, this precision facilitates ion measurements performed in one laboratory to be reproduced in another laboratory. In another aspect, this precision provides a greater degree of confidence in acquired measurements using the AC-SLIMS apparatus and methods. In a further aspect, this precision is important for detailed examination of ion structure, as it allows for reasonable determinations of what different structures may be present in a sample. In an additional aspect, as the collision cross-section may be used in other calculations as a physical constant, this precision lends itself to further precision in those other calculations as well.

The discussion will now turn to FIG. 1, which presents a schematic diagram of an apparatus 100 for ion mobility separations, in accordance with one embodiment of the present disclosure. The apparatus 100 includes at least one surface (not shown) and a plurality of electrodes coupled thereto. In certain embodiments, the at least one surface is a single surface. In further embodiments, the at least one surface is a single planar surface or a single non-planar surface (e.g., a curved surface). In alternative embodiments, the at least one surface is a pair of surfaces, oriented approximately parallel to one another and offset by a gap (e.g., vertically offset).

For example, in certain embodiments, a pair of surfaces may be approximately parallel if a spacing between the pair of surfaces along their respective lengths deviates from a selected value by less than a pre-determined amount. The predetermined amount may be selected within the range from 0.001% to 10%.

In an embodiment, the at least one surface is a substrate formed from a material suitable for receiving one or more electrically conductive elements (e.g., electrodes) and/or forming electrical circuits thereon. For example, the at least one surface may be formed from any insulating material (e.g., a semiconductor, a ceramic, a polymer, etc.). In another example, the at least one surface may be formed by additive manufacturing process (e.g., 3-D printing).

In further examples, the at least one surface is a printed circuit board (PCB). PCBs may be formed from materials including, but not limited to, reinforced or unreinforced polymer resins. Example reinforcements may include, but are not limited to, continuous and discontinuous fibers (e.g., glass fibers). Example polymer resins may include, but are not limited to, epoxies.

In further embodiments, the dimensions of the at least one surface may be provided, as necessary, without limit. In certain embodiments, each of the dimensions of the at least one surface may be independently selected from the range of 3 cm-300 cm in length and 0.75 cm-76 cm in width.

The plurality of electrodes includes a first plurality of continuous electrodes 110 and 120 and a second plurality of 125 of segmented electrodes. A plurality of guard electrodes 130 are also positioned to the side of the first plurality of continuous electrodes 110 and 120. As discussed in greater detail below, the first plurality of continuous electrodes 110, 120 serve to confine the ions in the y-direction (e.g., vertically), while the guard electrodes 130 serve to confine the ions in the x-direction (e.g., in the width direction). The second plurality of segmented electrodes 125 form the TW that moves the ions in the z-direction (e.g., in the longitudinal direction) through the apparatus 100.

The discussion will continue with further reference to the first plurality of continuous electrodes 110, 120. As an initial matter, these electrodes may be interchangeably referred to herein as RF electrodes, first plurality of electrodes, or simply electrodes 110 and/or electrodes 120. Each of the first plurality of electrodes 110, 120 is generally elongated and continuous, extending along at least a portion of a length of the at least one surface (e.g., the z-direction). For example, as illustrated in FIG. 1, each of the first plurality of electrodes 110, 120 extends along the entire length of the surface. Further, the first plurality of electrodes 110 and 120 are positioned in an alternating fashion along a width of the surface (e.g., the x-direction), spaced apart from one another.

The dimensions of the first plurality of electrodes 110, 120, and their respective spacing to one another, may be independently selected to generate effective potentials that confine ions within the apparatus 100. In general, there is no maximum or minimum length or width of the first plurality of electrodes 110, 120. The length of the first plurality of electrodes 110, 120 is limited only by the desired dimensions of the at least one surface upon which they are secured. The width and lateral spacing of the first plurality of electrodes 110, 120 is generally desired to be as small as feasible to provide fine control of the confining electric field. In an example, the width of the first plurality of electrodes 110, 120 may be independently selected from the range of 0.05 mm to 5 mm (e.g., 0.5 mm). In a further example, the lateral spacing between adjacent electrodes of the first plurality of electrodes 110, 120 may be selected from the range of 0.04 mm-4 mm.

It should be noted that the embodiment of FIG. 1 is not be construed as limiting, and that the number of first plurality of continuous electrodes 110 and 120 coupled to the at least one surface can be the same or different. Also, the first plurality of continuous electrodes nearest the guard electrodes 130 can each be the same electrode 110 or 120 or can each be different ones of the first plurality of electrodes 110 and 120. Thus, as one example, the electrode nearest each guard electrode 130 can be the same electrode 110. Further alternative configurations of the first plurality of electrodes are discussed in greater detail below with respect to FIG. 6.

Each of the electrodes of first plurality of electrodes 110, 120 is additionally in electrical communication with an RF voltage source (not shown). In use, RF voltages are applied to laterally adjacent ones of the first set of electrodes 110 and 120, approximately 180° out of phase with respect to each other. That is, an RF voltage applied to the plurality of first electrodes 110 is 180° out of phase with an RF voltage applied to the plurality of first electrodes 120, as one example. Thus, the charge on laterally adjacent ones of the first plurality of electrodes 110 and 120 at any given time is of opposite polarity, indicated in FIG. 1 as RF+ and RF−. As discussed in detail below, as time advances, the polarity of each of the plurality of electrodes 110, 120 switches, transitioning from positive to negative or negative to positive.

An example of ion behavior within electric fields generated by application of RF voltages to the first set of electrodes 110 and 120 is illustrated in FIGS. 4A-4B. A longitudinal cross-section (x-y plane) of apparatus 100 is presented, including two opposing surfaces having respective first sets of electrodes 110 and 120 coupled thereto. In an initial state (FIG. 4A), electrodes 110 have a positive charge thereon and electrodes 120 have a negative charge thereon.

Assume, for example, first and second positive ions 400, 402 positioned between the two surfaces, with the first positive ion 400 positioned approximately in the middle of the two surfaces and the second positive ion (solid outline) positioned near an electrode 110. In general, the magnitude of the voltage applied to the first plurality of electrodes 110, 120 is such that the resultant electrical fields only influence the motion of the ions when the distance between the ion and the electrode is less than two electrode widths. This creates a "neutral zone" (dot-dot-dash lines) between the surfaces where the first positive ion experiences approximately no net attraction or repulsion due to the electric fields generated by the first plurality of electrodes 110, 120. In contrast, the second positive ion, which is close to positively charged electrode 110, experiences a repulsive force urging the second positive ion towards the neutral zone (e.g., upwards in FIG. 4A).

With further reference to FIG. 4, as time advances, the c of the first set of electrodes 110, 120 reverses, resulting in the electrodes 110 possessing a negative charge and the electrodes 120 possessing a positive polarity. Should the repulsive force experienced by the second positive ion, as described above with respect to FIG. 4A, cause it to move beyond the neutral zone, the electric field generated by the electrode 120 exerts a further repulsive force urging the second positive back towards the neutral zone (e.g., upwards in FIG. 4A).

Subsequently, as time further advances, the polarity of the first plurality of electrodes 110, 120 reverses again, returning to the state of FIG. 4A. Provided that the RF frequency changes quickly enough to prevent ions from contacting the electrodes, the position of ions that stray out of the neutral zone close is corrected to return them to the neutral zone, providing confinement between the two surfaces (i.e., in the y-direction). For example, in an embodiment, the frequency of the RF voltage applied to the first plurality of electrodes may be selected from the range between 100 kHz-5 MHz. the amplitude of the RF voltage may be selected from the range between 10 V to 500 V.

For a given charge, the RF frequency and amplitude are selected from their respective ranges based upon the mass of the ions and the pressure of the buffer gas. Relatively higher frequencies and higher amplitudes are selected for relatively light ions (i.e., faster moving ions) and lower frequencies and lower amplitudes selected within this range for relatively heavy ions (i.e., slower moving ions). Relatively higher voltages are employed for higher pressures. The electric field generated by the RF electrodes in this manner may be represented by an effective electric field, $E_{\mathit{eff, RF}}$, as illustrated in FIG. 4C.

With further reference to FIG. 1, each of the plurality of guard electrodes 130 is coupled to the surface and positioned laterally adjacent to the outward most ones of the first plurality of electrodes 110, 120. For example, as illustrated in FIG. 1, the plurality of guard electrodes 130 are positioned laterally adjacent to the outward most electrodes 110. Each of the plurality of guard electrodes 130 are further in electrical communication with a DC voltage source (not shown). Each of the dimensions of the guard electrodes may be independently selected from the range of 0.05 mm-5 mm in width.

In use, a constant DC voltage is applied to each of the plurality of guard electrodes 130 to further confine ions in the x-direction (e.g., laterally, orthogonal to the direction of longitudinal motion of the ions). The polarity of the DC voltage is selected to be the same as that of the ions, generating an electric field, $E_{DC}$ that repels the ions, as illustrated in FIG. 4C. In an embodiment, the magnitude of the DC voltage is selected from the range between 1 V to 100 V.

The discussion will now turn to the second plurality of electrodes 125 with further reference to FIG. 1. The electrodes of the second plurality of electrodes 125 are segmented and interposed between the first plurality of electrodes 110 and 120. A given set of electrodes of the second plurality of electrodes 125 may include respective electrodes positioned between a given pair of the first plurality of electrodes 110, 120. For example, a given set of electrodes of the second plurality of electrodes 125 may extend in the z direction along a line, as illustrated in FIG. 1. Each of the dimensions of the respective ones of the second plurality of electrodes 125 may be independently selected from the range of 0.2 mm-20 mm in length and 0.04 mm-4.5 mm in width.

It may be understood, however, that other configurations of the second plurality of electrodes are also contemplated. For example, a set of the second plurality of electrodes may be positioned laterally adjacent to the guard electrodes, and thus not necessarily be interposed between laterally adjacent ones of the first plurality of electrodes. In other embodiments, the length of respective ones of the second plurality of electrodes may be independently varied. Further alternative configurations of the second plurality of electrodes are discussed in greater detail with respect to FIG. 6.

Figure 5:
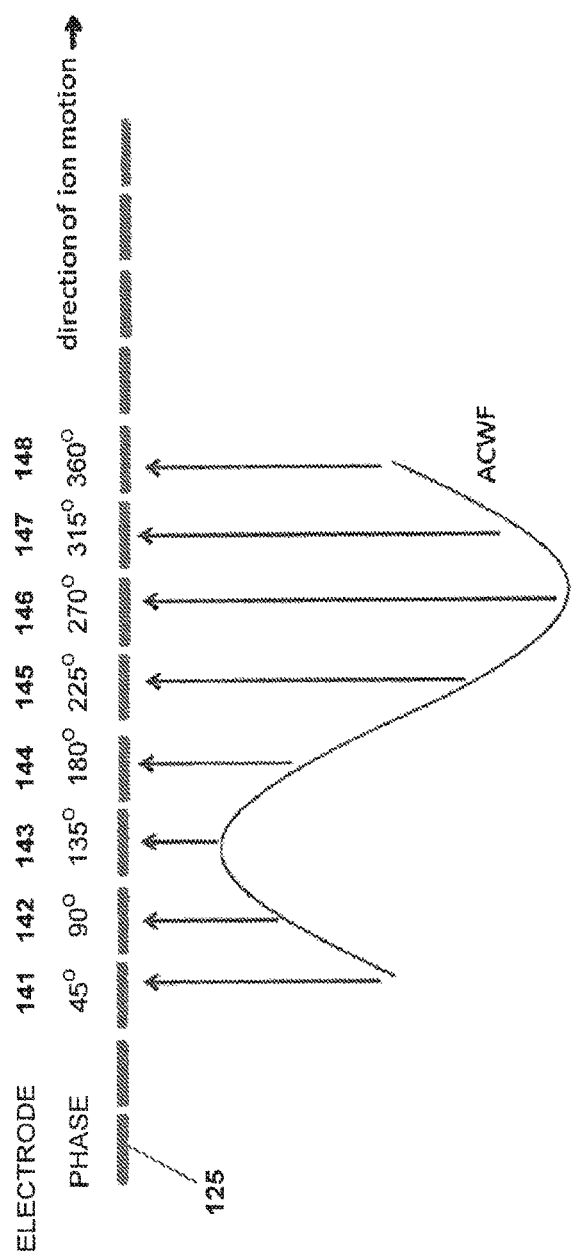
FIG. 5 is a schematic illustration of a continuous AC voltage waveform (ACWF) applied to a second plurality of segmented electrodes for generating a traveling wave for axial movement and separation of ions.

Each of the segmented electrodes of the second plurality of electrodes 125 is further in electrical communication with an AC voltage source (not shown). With further reference to FIG. 5, a single set of the second plurality of electrodes 125 is illustrated. In use, an AC voltage waveform is applied to each of the electrodes 125, with the AC voltage waveform applied to longitudinally adjacent electrodes within the longitudinal set of the second plurality of electrodes 125. The applied AC voltage waveform is phase shifted with respect to the longitudinally adjacent electrodes 125. In this manner, the applied AC voltage waveform spans a portion of the second plurality of electrodes 125, extending longitudinally in the desired direction of ion travel (i.e., the z-direction).

For example, as illustrated in FIG. 5, the second plurality of electrodes 125 includes 8 segmented electrodes 141-148 across which an AC voltage waveform in the form of a sine wave is applied. In an embodiment, the phase shift between each of the segmented electrodes 141-148 is equal (i.e., 45°)

and the total phase shift across the electrodes 141-148 sums to 360°. That is, the phases of the applied AC waves are shifted by 45°, 90°, 135°, 180°, 225°, 270°, 315°, and 360° respectively on the segmented electrodes in a stepwise fashion so as to move and separate the ions in the direction of the increasing phase shift. Accordingly, the AC voltage waveform applied to segmented electrode 141 has a phase of 45°; the AC voltage waveform applied to segmented electrode 142 has a phase of 90°; the AC voltage waveform applied to segmented electrode 143 has a phase of 135°; the AC voltage waveform applied to segmented electrode 144 has a phase of 180°; the AC voltage waveform applied to segmented electrode 145 has a phase of 225°; the AC voltage waveform applied to segmented electrode 146 has a phase of 270°; the AC voltage waveform applied to segmented electrode 147 has a phase of 315°; and the AC voltage waveform applied to segmented electrode 148 has a phase of 360°.

Subsequently, the AC voltage waveform is applied in a repeating and stepwise manner to the plurality of second electrodes that follow electrodes 141-148. For example, with further reference to FIG. 1, the AC voltage waveform applied to segmented electrode 151 has a phase of 45°; the AC voltage waveform applied to segmented electrode 152 has a phase shift of 90°; the AC voltage waveform applied to segmented electrode 153 has a phase shift of 135°; the AC voltage waveform applied to segmented electrode 154 has a phase shift of 180°; the AC voltage waveform applied to segmented electrode 155 has a phase shift of 225°; the AC voltage waveform applied to segmented electrode 156 has a phase shift of 270°; the AC voltage waveform applied to segmented electrode 157 has a phase shift of 315°; and the AC voltage waveform applied to segmented electrode 158 has a phase shift of 360°. This process is repeated for additional segmented electrodes of the second plurality of electrodes 125 until the end of the second plurality of electrodes 125 is reached, so as to move and separate the ions in the z-direction.

At a given time, an ion within the apparatus 100 is generally located at the lowest energy position, which depends upon the ion velocity to keep up with the traveling wave motion. For example, assume this lowest energy position lies at or near to the position of the segmented electrode having the lowest magnitude of the AC voltage waveform (i.e., electrode segment 146 having a phase shift of 270°). When the maximum ion velocity is approximately equal to the speed of the traveling wave, $c \approx 1$, ions can move with the wave much of the time, but are also occasionally passed over by waves. Ions of lower velocity or mobility tend to fall behind more often than those of higher velocity or mobility, and ion separation is achieved. Thus, under the conditions of $c \approx 1$, translation of the AC voltage waveform in the z-direction forms a traveling wave that urges the ion to move so as to stay within the lowest energy position.

In an embodiment, the frequency of the AC voltage waveform may be selected from the range between 10 Hz-200 kHz (e.g., 1 kHz-200 kHz) and the amplitude of the AC voltage waveform may be selected from the range between 1 V to 200 V. For example, in one embodiment, the frequency of the AC voltage waveform can be selected from the range of 1 Hz-1 kHz. In further embodiments, the pressure of the carrier gas is selected from the range of atmospheric pressure to 1 mtorr vacuum. For a given charge, the frequency and amplitude of the AC voltage waveform are selected from their respective ranges based upon one or more of pressure of the buffer gas, dimensions of the segmented electrodes of the second plurality of electrodes 125, and the mass to charge ratio of the ions.

The embodiment of FIG. 5 employs a constant phase shift of 45° between neighboring segmented electrodes (i.e., 360° divided by the number of electrodes over which the AC voltage waveform is spread). However, in further embodiments, the traveling AC voltage waveform may adopt other phase shifts, selected from the range of 0°-359°, without limit. For example, one alternative embodiment, the phase shift may be 90° or 120°. In other alternative embodiments, the phase shift between at least one pair of neighboring segmented electrodes may be different. In further alternative embodiments, AC voltage waveform exhibits at least one discontinuity (i.e., the sum of phase shifts between the electrodes over which the AC voltage waveform is spread does not sum to 360°).

In the example of FIG. 5, the AC voltage waveforms are sine waves. However, it may be understood that, in alternative embodiments, the AC voltage waveforms may adopt other forms, such as cosine waves or sums of more than one wave.

In additional embodiments, the number of segmented electrodes of the second plurality of electrodes may be different than that illustrated in FIG. 1 or 5. For example, the plurality of second electrodes require a minimum of three segmented electrodes in order to form a potential valley to trap and transport ions for separation. However, there is no limit on the maximum number of electrodes within the plurality of second electrodes. Accordingly, the number of electrodes within the plurality of second electrodes may be selected from integers greater than or equal to three.

Figure 2:
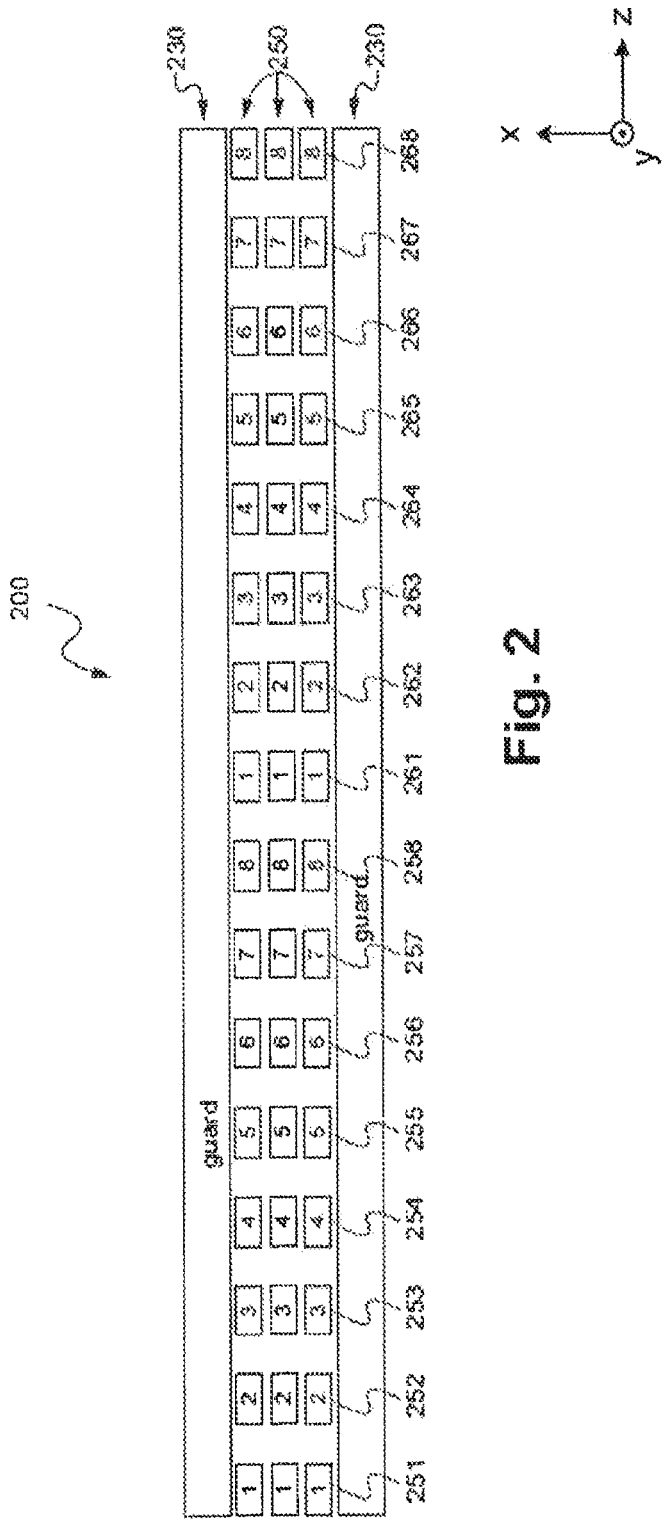
FIG. 2 is a schematic diagram of an apparatus for ion mobility separations, in accordance with a second embodiment of the present disclosure.

Turning now to FIG. 2, a schematic diagram of an apparatus 200 for ion mobility separations, in accordance with a second embodiment of the present disclosure, is illustrated. The apparatus 200 includes at least one surface (not shown), and a plurality of segmented electrodes 250 coupled to the surface. In alternative embodiments, the at least one surface is a pair of surfaces, oriented parallel to one another and offset by a gap (e.g., vertically offset). The apparatus 200 further includes guard electrodes 230 are positioned to the side of the plurality of electrodes 250.

Still referring to FIG. 2, the apparatus 200 differs from the apparatus 100 in that AC and RF voltages are applied concurrently on the plurality of electrodes 250, rather than on the first plurality of electrodes 110, 120 and the second plurality of electrodes 125. Thus, as discussed in greater detail below, the plurality of segmented electrodes 250 serve to confine the ions in the y-direction (e.g., vertically) and form the TW that moves the ions in the z-direction (e.g., longitudinally) through the apparatus 100. The plurality of guard electrodes 130 serve to confine the ions in the x-direction (e.g., horizontally). Unless otherwise noted in the discussion below, the apparatus 200 operates similarly to apparatus 100.

Each of the plurality of segmented electrodes 250 is in electrical communication with an AC voltage source and an RF voltage source (not shown). With further reference to FIG. 2, in use, AC voltages are applied to each of the plurality of segmented electrodes 250, with the AC voltages applied to longitudinally adjacent segmented electrodes being phase shifted with respect to one another by a value selected from the range of 0°-359°. In this manner, an AC voltage waveform is formed that spans a portion of the plurality of segmented electrodes 250, extending longitudinally in the desired direction of ion travel (i.e., the z-direction). Concurrently, RF voltages are superimposed upon the applied AC voltages. The phase of the RF voltages applied to longitudinally adjacent segmented electrodes being approximately 180° out of phase with respect to one another (i.e., the phase shift is in the direction of ion motion).

For example, an AC voltage waveform exhibiting a 45° phase and a separate RF voltage are each applied to electrode segment 251; an AC voltage waveform exhibiting a 90° phase and an RF voltage, 180° out-of-phase from the RF voltage applied to the electrode segment 251, are each applied to the electrode segment 252; an AC voltage waveform exhibiting a 135° phase and an RF voltage, 180° out-of-phase from the RF voltage applied to the electrode segment 252, are each applied to the electrode segment 253; an AC voltage waveform exhibiting a 180° phase and an RF voltage, 180° out-of-phase from the RF voltage applied to the electrode segment 253, are each applied to the electrode segment 254; an AC voltage waveform exhibiting a 225° phase and an RF voltage, 180° out-of-phase from the RF voltage applied to the electrode segment 254, are each applied to the electrode segment 255; an AC voltage waveform exhibiting a 270° phase and an RF voltage, 180° out-of-phase from the RF voltage applied to the electrode segment 255, are each applied to the electrode segment 256; an AC voltage waveform exhibiting a 315° phase and an RF voltage, 180° out-of-phase from the RF voltage applied to the electrode segment 256, are each applied to electrode segment 257; and an AC voltage waveform exhibiting a 360° phase and a RF voltage, 180° out-of-phase from the RF voltage applied to electrode segment 257, are each applied to electrode segment 258.

Continuing on the segmented electrodes in FIG. 2, an AC voltage waveform exhibiting a phase shift of 45° and an RF voltage are concurrently applied to segmented electrode 261; an AC voltage waveform exhibiting a phase of 90° and an RF voltage, 180° out-of-phase from the RF voltage applied to electrode 261, are each applied to segmented electrode 262; an AC voltage waveform exhibiting a phase of 135° and an RF voltage, 180° out-of-phase from the RF voltage applied to electrode 262, are each concurrently applied to segmented electrode 263; an AC voltage waveform exhibiting a phase of 180° and an RF voltage, 180° out-of-phase from the RF voltage applied to electrode 263, are each concurrently applied to segmented electrode 264; an AC voltage waveform exhibiting a phase of 225° and an RF voltage, 180° out-of-phase from the RF voltage applied to electrode 264, are each concurrently applied to segmented electrode 265; an AC voltage exhibiting a phase of 270° and an RF voltage, 180° out-of-phase from the RF voltage applied to electrode 265, are each concurrently applied to segmented electrode 266; an AC voltage waveform exhibiting a phase of 315° and an RF voltage, 180° out-of-phase from the RF voltage applied to electrode 266, are each concurrently applied to segmented electrode 267; and an AC voltage waveform exhibiting a phase of 360° and an RF voltage, 180° out-of-phase from the RF voltage applied to electrode 267, are each concurrently applied to segmented electrode 268.

In an embodiment, the frequency of the RF voltage may be selected from the range between 100 kHz-5 MHz and the amplitude of the RF voltage may be selected from the range between 10 V to 500 V. In further embodiments, the frequency of the AC waveform may be selected from the range between 10 Hz-200 kHz and the amplitude of the AC waveform may be selected from the range between 1 V to 200 V.

With further reference to FIG. 2, each of the plurality of guard electrodes 230 is coupled to the surface, positioned laterally adjacent to the outward most ones of the plurality of segmented electrodes 250. Each of the plurality of guard electrodes 230 are further in electrical communication with a DC voltage source (not shown). In use, a constant DC voltage is applied to each of the guard electrodes 230 to further confine ions in the x-direction (e.g., laterally, orthogonal to the direction of longitudinal motion of the ions), as discussed above with respect to the guard electrodes 130 of FIG. 1. In an embodiment, the magnitude of the DC voltage is selected from the range of 1 V to 100 V.

The example above employs a constant phase shift of 45° between the AC voltage waveform applied to longitudinally adjacent ones of the plurality of segmented electrodes 250 (i.e., 360° divided by the number of electrodes over which the AC waveform is spread). However, in further embodiments, the traveling AC voltage waveform may adopt other phase shifts, selected from the range of 0°-359°, without limit. For example, in one alternative embodiment, the phase shift may be 90° or 120°. In other alternative embodiments, the phase shift between at least one pair of longitudinally adjacent segmented electrodes may be different. In further alternative embodiments, AC voltage waveform may exhibit at least one discontinuity (i.e., the sum of phase shifts between the electrodes over which the AC voltage waveform is spread does not sum to 360°).

In additional embodiments, the number of the plurality of segmented electrodes 250 may be different than that illustrated in FIG. 2. For example, the plurality of segmented electrodes 250 requires a minimum of three segmented electrodes in order to form a potential valley to trap and transport ions for separation. However, there is no limit on the maximum number of segmented electrodes of the plurality of segmented electrodes. Accordingly, the number of segmented electrodes may be selected from integers greater than or equal to three.

The AC voltage waveforms applied to the plurality of electrodes of the apparatus of FIG. 2 have been discussed above as sine waves the AC voltage waveforms. However, in further embodiments, the AC voltage waveform may adopt other forms, such as cosine waves or sums of more than one wave.

Figure 3:
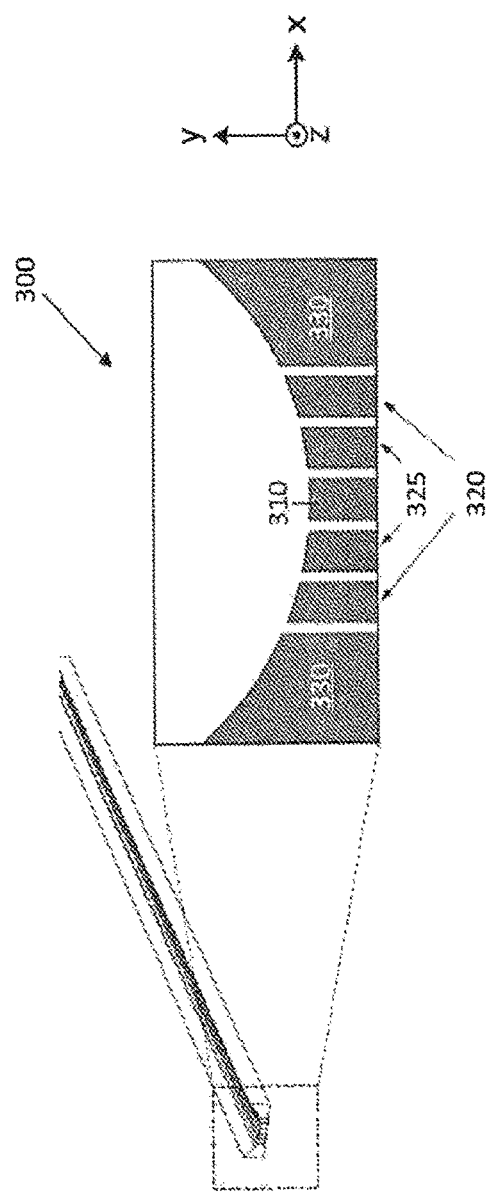
FIG. 3 is a schematic illustration of an apparatus for ion mobility separations, in accordance with a third embodiment of the present disclosure.

With reference to FIG. 3, a schematic diagram for an apparatus 300 for ion mobility separations, in accordance with a third embodiment of the present disclosure, is illustrated. The apparatus 300 includes at least one surface (not shown), and a plurality of curved electrodes 310, 320, 325, and 330 coupled to the surface. The radius of curvature of the curved electrodes may be selected from the range of 1 mm to 100 mm.

A first plurality of curved electrodes 310 and 320 are laterally spaced from one another and in electrical communication with an RF voltage source (not shown) In operation, opposite phase RF voltages is are applied to laterally adjacent ones of the first plurality of electrodes 310 and 320 to confine the ions within the y-direction. The dimensions and positioning of the curved electrodes 310, 320, as well as the manner of applying the RF voltages, may be provided as discussed above with respect to the first plurality of electrodes 110, 120 of FIG. 1.

Electrodes 330 are curved guard electrodes, laterally spaced from one another and adjacent the outermost ones of the curved electrodes 310, 320, and 325. For example, as illustrated in FIG. 3, the curved guard electrodes 330 are positioned laterally adjacent to the outermost ones of the first plurality of curved electrodes 310, 320. The curved guard electrodes 330 are further in electrical communication with a DC voltage source (not shown). In operation, DC voltages are applied to the guard electrodes 330 such that the curved shape and the electric fields generated by the applied DC potentials provides confinement of the ions in the x-direction. The dimensions and positioning of the curved guard electrodes 330, as well as the manner of applying the DC voltages, may be provided as discussed above with respect to guard electrodes 130 of FIG. 1.

A second plurality of curved electrodes 325 are segmented and interposed between respective ones of the first plurality of curved electrodes 310, 320. The second plurality of curved electrodes are further in electrical communication with an AC voltage source (not shown). A given set of electrodes of the second plurality of curved electrodes 325 may be positioned between a given pair of the first plurality of curved electrodes 310, 320. In operation, a continuous AC voltage waveform is applied to a second plurality of curved electrodes 325, where the AC voltage waveform is phase shifted on longitudinally adjacent electrodes within a given set of the second plurality of curved electrodes to move the ions through the length of the apparatus 300 (i.e., in the z-direction). The dimensions and positioning of the second plurality of curved electrodes 325, as well as the manner of applying the continuous AC voltages, may be provided as discussed above with respect to the second plurality of electrodes 120 of FIG. 1.

Alternative embodiments of electrode configurations coupled to the at least one surface are illustrated in FIGS. 6A-6F. As discussed below, the embodiments of FIGS. 6A-6F are presented in the context of apparatus 100 with reference to the first plurality of continuous electrodes 110, 120, guard electrodes 130, and the second plurality of electrodes 125. Furthermore, the guard electrodes 130 are positioned to the side of the first plurality of electrodes 110 and 120 and the second plurality of segmented electrodes 125 is interposed between the first plurality of electrodes 110 and 120.

In alternative embodiments, the positions of the first plurality of continuous electrodes 110, 120 and the second plurality of segmented electrodes 125 in the electrode configurations of FIGS. 6A-6F may be reversed. In further alternative embodiments, the electrode configurations of FIGS. 6A-6F may be also used in combination with the apparatus 200, where the plurality of electrodes 250 are provided in lieu of the first and second plurality of electrodes 110, 120, 125.

FIG. 6A illustrates an embodiment of an alternative electrode configuration including first segments 600A-1 oriented parallel to one another and connected to a second segment 600A-2 oriented perpendicular the first segments 600A-1, forming a "U" shape. This configuration may be beneficial in circumstances where it is desired to reverse the direction of ion motion. It may be understood that, in further alternative embodiments, the respective orientations of the first and second segments 600A-1, 600A-2 may be varied. For example, the first segments 600A-1 need not be parallel but may adopt a non-zero angle with respect to one another. In another example, the second segment 600A-2 need not be perpendicular to one or both of the first segments 600A-1 and may instead adopt a non 90° angle, while still remaining connected to each of the first segments 600A-1.

FIG. 6B illustrates an embodiment of an alternative electrode configuration where each of first plurality of electrodes 110, 120 includes a first portion, adjacent the guard electrodes 130, that is oriented with its longitudinal axis parallel to the direction of ion travel and a second portion, inward of the first portion, that is oriented perpendicular to the direction of ion travel. Each of the second plurality of electrodes 125 is oriented with its longitudinal axis perpendicular to the direction of ion travel. The manner of applying the RF and AC waveforms to the first and second plurality of electrodes is the same as that discussed above with respect to FIG. 1.

FIG. 6C illustrates an embodiment alternative electrode configuration that varies the electrode arrangement along the path length of ion travel. The electrode configuration of FIG. 6C includes a first segment 600C-1 and a second segment 600C-2. In the first segment 600C-1, the longitudinal axis of each of the first plurality of electrodes 110, 120 and the second plurality of electrodes are each oriented parallel to the direction of ion travel (i.e., longitudinally). In the second segment 600C-2, the first and second plurality of electrodes 110, 120, 125 are configured as discussed above with respect to FIG. 6B.

Figure 6D:
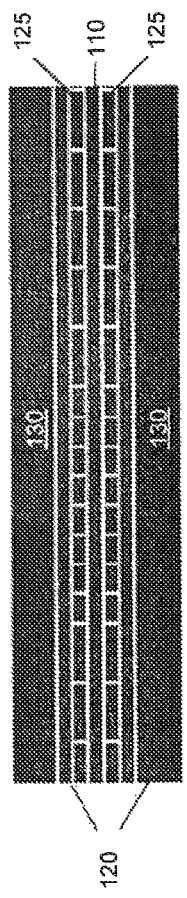
Figure 6E:
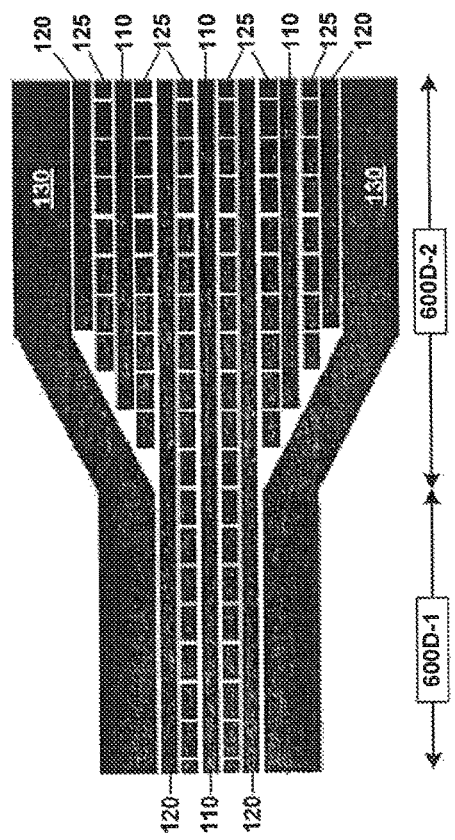

FIG. 6E illustrates an embodiment of an alternative electrode configuration including a first portion 600D-1 having fewer of the first and second plurality of electrodes 110, 120, 125 than a second portion 600D-2. The result is that the width of the ion pathway along the direction of motion of the ions is varied (e.g., converging, diverging, etc.) along the direction of ion motion. This configuration may be beneficial for compressing the width of the ion beam (e.g., for focusing) and/or adjacent to the junction of two different ion pathways.

Figure 6F:
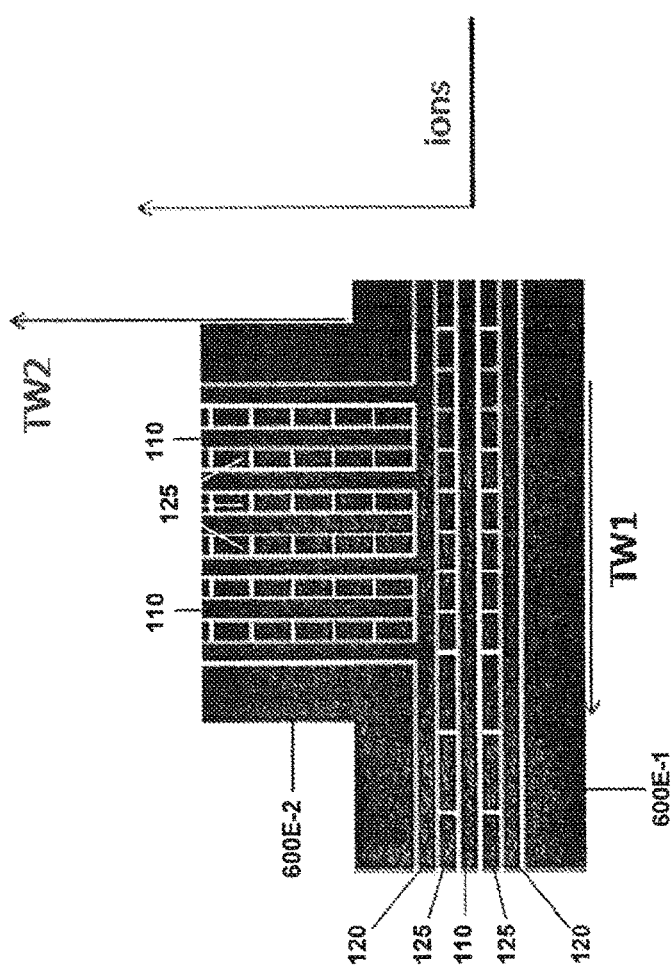

FIG. 6F illustrates an embodiment of an alternative electrode configuration including a first segment 600E-1 connected to a second segment 600E-2 at a right angle, forming a "T" shape. This configuration may be beneficial in circumstances where it is desired to divert ions from the first segment 600E-1 to the second segment 600E-2. This configuration may be desirable for selection of ions of a particular mobility or composition (e.g., removal of unwanted ions prior to injection of the remaining ions within a mass spectrometer).

It may be understood that, in further alternative embodiments, the respective orientations of the first and second segments 600E-1, 600E-2 may be varied. For example, the first segment 600E-1 need not be perpendicular to the second segment 600E-2 but may adopt a non-90° angle.

Figures 6G, 6H:
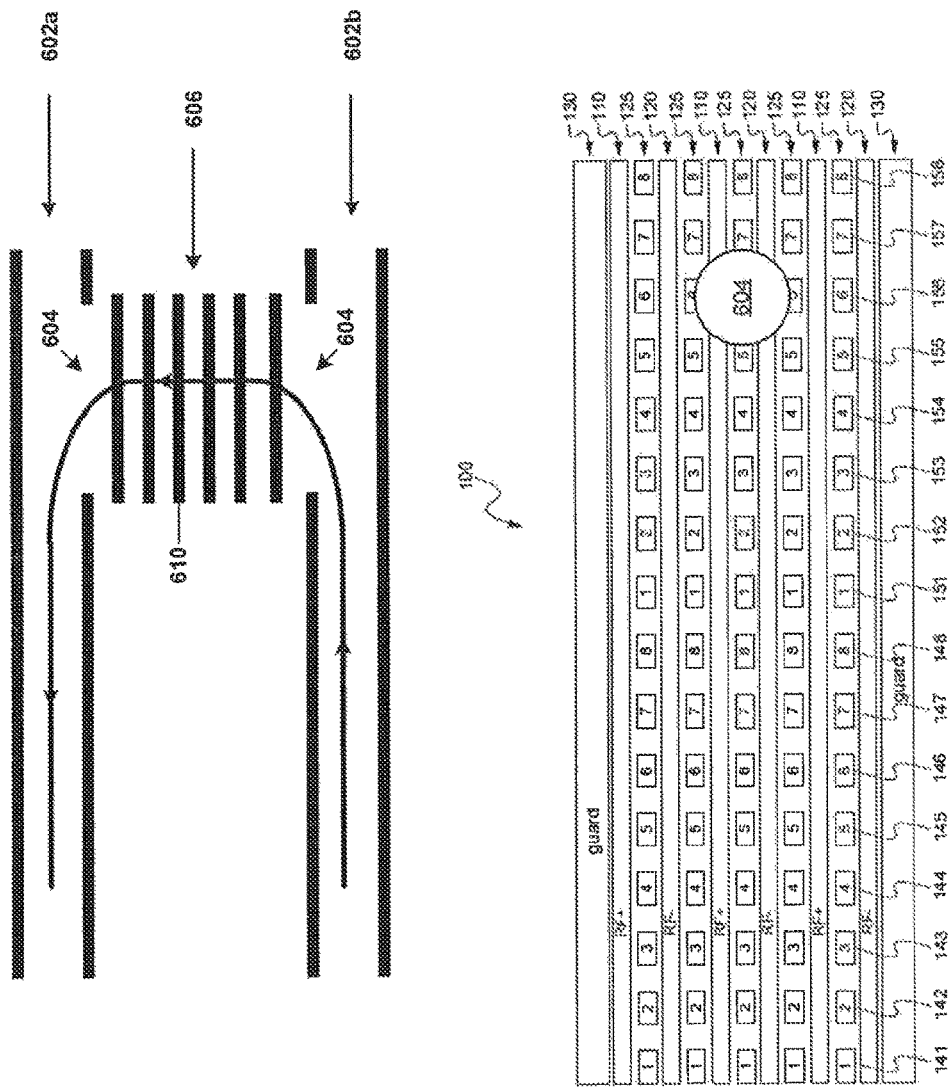

FIG. 6G illustrates an apparatus containing two different levels 602a, 602b, where each level includes a pair of parallel surfaces containing the plurality of electrodes (e.g., 110, 120, 125), as discussed above. In one aspect, the use of multiple levels allows different levels to be optimized for separation of different ions.

Notably, however, a mechanism of transporting ions between levels is necessary to insert and remove ions from the respective levels. Accordingly, an opening 604 (e.g., a square or circular opening) is formed each of the opposing parallel surfaces of levels 602a, 602b. The opening 604 is positioned so as to intersect second plurality of segmented electrodes 125 (e.g., FIG. 6H), allowing access to an elevator 606. An elevator 606 is positioned so as to overlap the respective openings 604 of levels 602a, 602b and includes a plurality of stacked, segmented electrode arrays 610 (e.g., 6 stacked electrodes). In operation, a traveling wave generated by the second plurality of electrodes 125 is employed to convey ions from the level 600a, through the elevator 606, to the level 600b, as illustrated by the directional arrows in FIG. 6G.

Figure 6J:
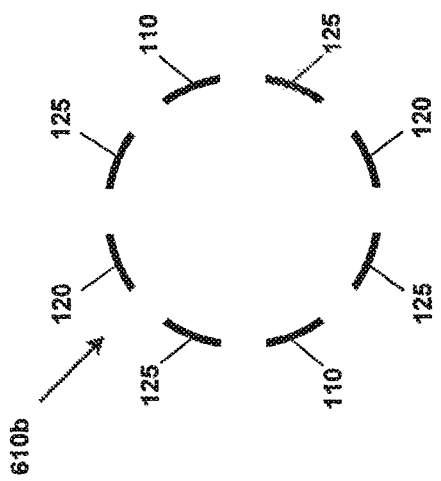
Figure 6I:
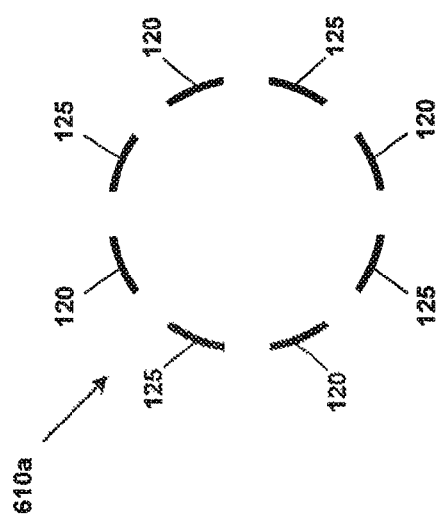

Embodiments of electrode arrays 610 within each electrode stack 610 are illustrated in FIGS. 6I and 6J. In general, each electrode array includes alternating AC electrodes (e.g., 125) and RF electrodes (110 and/or 120). In one embodiment, each of the RF electrodes within an electrode array 610a may each possess the same polarity at a given time. In an alternative embodiment, each of the RF electrodes within an electrode array 610b may each possess the opposite polarity as its nearest neighbor RF electrode. For example, as illustrated in FIG. 6I, electrode array 610a includes alternating segments of RF electrodes 120 and AC electrodes 125, where the RF electrodes 120 each have the same RF phase at a given time. As further illustrated in FIG. 6J, electrode array 610b includes alternating segments of RF electrodes 110, 120, and AC electrodes 125, where the RF electrodes 110 and 120 have the opposite RF phase (i.e., are 180° out-of-phase with each other).

Embodiments of elevators 606 having different stacking arrangements of electrode arrays 606 are illustrated in FIGS. 6K and 6L. For example, the elevator 606a of FIG. 6K is formed from electrode arrays 606a, where each RF electrode within a given electrode array 606a possesses the same polarity. Notably, though, neighboring electrode arrays 606 possess opposite polarities. In contrast, the elevator 606b of FIG. 6L is also formed from electrode arrays 506a but neighboring electrode arrays 606a also possess the same polarities.

Figure 6M:
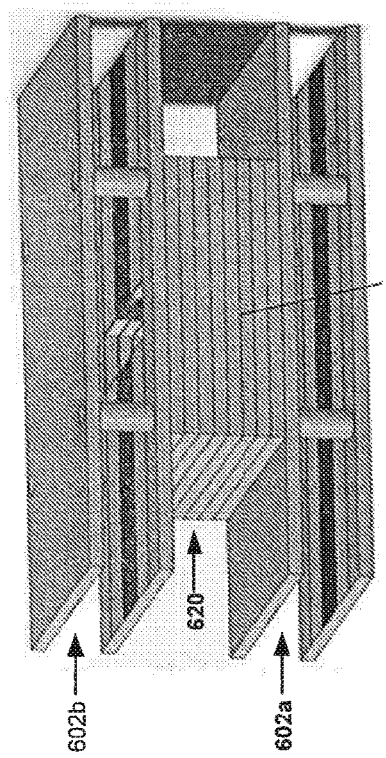
Figure 6O:
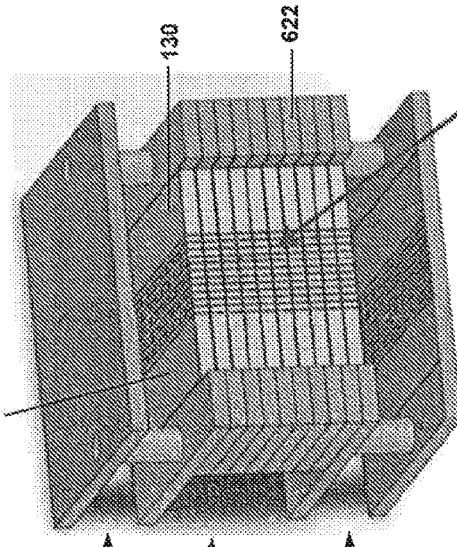
Figure 6N:
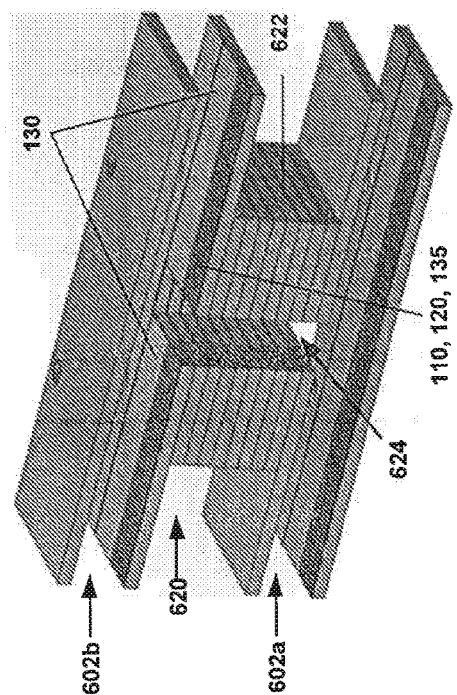

In an alternative embodiment, the apparatus 100 includes an elevator 620, as illustrated in FIGS. 6M-6O. The elevator 620 is formed from a plurality of plates 622, each having electrodes 110, 120, 125, and 130, that are stacked upon one another. Each plate 622 contains an aperture 624 that is aligned with an aperture 624 of its adjacent neighbor, forming a passage for ion transit through the elevator 620. As above, a traveling wave generated by the plurality of second electrodes 125 is employed to convey ions from the level 600a, through the elevator 620, to the level 602b, while electric fields generated by RF electrodes 110, 120 and guard electrodes 130 confine the ions within the aperture 622 of their respective plate 622.

Figure 6P:
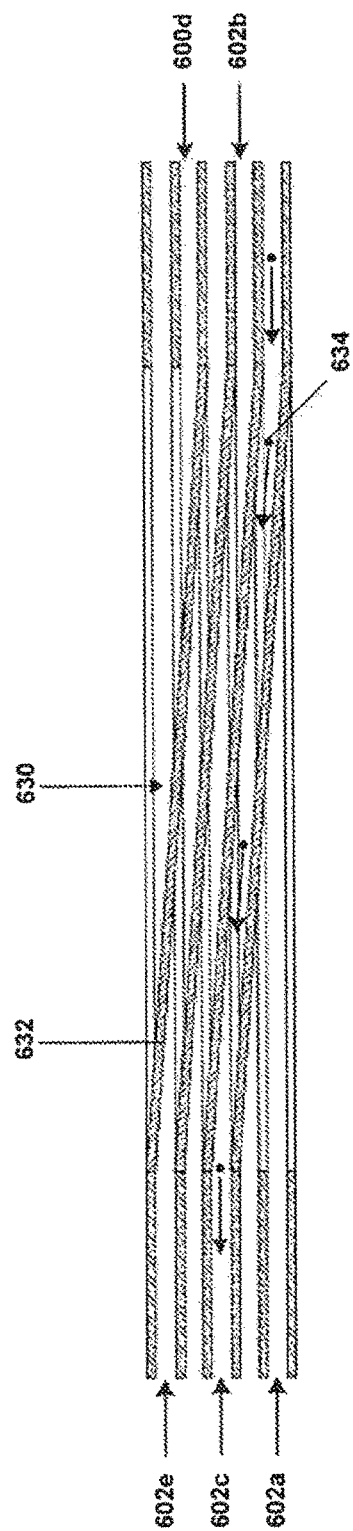

In a further alternative embodiment, illustrated in FIG. 6P, the apparatus 100 includes at least two levels 602 formed and connected by relatively inclined portions 630, where each of the levels 602 and the inclined portions 630 include pairs of parallel surfaces containing the plurality of electrodes 110, 120, 125, 130. For example, as illustrated in FIG. 6P, five levels 602a-602e are present, where level 602a is the lower-most level and level 602e is the upper-most level. Furthermore, the incline 630a extends between level 602a and 602c, incline 630b extends between level 602b and 602d, and incline 630c extends between levels 602c, and 602e. In use, a traveling wave generated by the plurality of second electrodes 125 is employed to convey ions (e.g., 634) from an underlying level (e.g., 602a, to an overlying level (e.g., level 602c) via respective inclines (e.g., 630a).

It may be understood that embodiments of each of the multi-level apparatus illustrated in embodiments of FIGS. 6G-6P may be employed with any configuration of electrodes, as illustrated in FIGS. 1, 2, 3 and 6A-6F.

EXPERIMENTAL RESULTS

Simulations were performed to explore the performance of embodiments of the AC-SLIMS approach discussed above for ion separation using flat and curved surfaces. Corresponding simulations are further performed for conventional TW-IMS using transient DC voltages for comparison. The following examples further serve to illustrate embodiments and aspects of the present disclosure and are not meant to be construed as limiting the scope thereof.

Example 1—Simulations of Flat Surfaces (i) AC-SLIMS Simulation Parameters

The schematic module shown in FIG. 1 is used for the simulation. The AC electrodes 125 are segmented electrodes adjacent to the long RF electrode strips 110, 120. The guard electrodes 130 are on the outside of the AC electrodes 125 and the RF electrodes 110, 120. The module is fabricated using PCBs and include of a pair of parallel PCBs (30.5 cm long×7.6 cm wide) spaced by a gap of 4.75 mm. The module uses 5 arrays of AC electrodes 125, separated from adjacent arrays of RF electrodes 110 and 120 by 0.13 mm. The dimensions of the AC electrodes 125 are 1.98 mm in length and 0.43 mm in width. Guard electrodes 130 are each 0.508 mm wide. The dimensions of the RF electrodes 110 and 120 are each 0.43 mm in width.

The module is operated at a pressure of 4 Torr utilizing nitrogen as the buffer gas. Singly charged ions with a mass to charge ratio (m/z) of 622 and 922 are used for the simulations.

RF voltages are applied to the six RF electrodes 110 and 120, 180° out-of-phase for adjacent electrodes on each surface to create the pseudopotentials to confine the ions and inhibit ion loss to the two PCBs.

AC voltage waveforms, sine waves in this simulation, are further applied to the first eight segmented electrodes 141, 142, 143, 144, 145, 146, 147, and 148 and the second set of eight segmented electrodes 151, 152, 153, 154, 155, 156, 157 and 158, positioned between the RF electrodes 110, 120.

A 45° phase shift of the AC voltage waveform is further employed to each adjacent electrode segments 141, 142, 143, 144, 145, 146, 147, and 148. The AC waveforms applied to longitudinally adjacent electrode segments 141, 142, 143, 144, 145, 146, 147, and 148 are shifted in phase in a repeating pattern. That is, the phases of the applied AC voltage waveform are shifted by 45°, 90°, 135°, 180°, 225°, 270°, 315°, and 360°, respectively, on the segmented electrodes 141, 142, 143, 144, 145, 146, 147, and 148 in a stepwise fashion so as to move and separate the ions in the direction of the increasing phase shift.

Subsequently, the AC voltage waveforms are further applied in a repeating and stepwise manner to the AC electrodes 151, 152, 153, 154, 155, 156, 157, and 158. The phases of the applied AC voltage waveform are shifted by 45°, 90°, 135°, 180°, 225°, 270°, 315°, and 360°, respectively, on the segmented electrodes 151, 152, 153, 154, 155, 156, 157, and 158 in a stepwise fashion so as to move and separate the ions in the direction of the increasing phase shift.

For additional arrays of segmented electrodes, the phase of the AC voltage waveform applied to those additional electrode arrays would repeat in a stepwise fashion so as to move and separate the ions in the direction of the increasing phase shift.

(ii) DC-TW Simulation Parameters

The schematic module 700 shown in FIG. 7A is used for the simulation. The DC electrodes 625 are segmented electrodes, positioned adjacent to the long RF electrodes 710, 720. The guard electrodes 730 are on the outside of the DC electrodes 725 and the RF electrodes 710, 720.

The module 700 is fabricated using PCBs and included of a pair of parallel PCBs (30.5 cm long×7.6 cm wide) spaced by a gap of 4.75 mm. The module used 5 arrays of DC electrodes 725, separated from adjacent arrays of RF electrodes 610 and 120 by 0.13 mm. The dimensions of the DC electrodes 725 were 1.98 mm in length and 0.43 mm in width. Guard electrodes 730 were 0.508 mm wide. The dimensions of the RF electrodes 710 and 720 were each 0.43 mm in width.

The module is operated at a pressure of 4 Torr utilizing nitrogen as the buffer gas. Singly charged ions with mass to charge (m/z) of 622 and 922 are used for the simulations.

RF voltages, are applied to the six RF electrodes 710 and 720, 180° out-of-phase for adjacent RF electrodes on each surface to create the pseudopotentials to confine the ions and inhibit ion loss to the two PCBs. The transient DC voltage waveform is applied to a series of adjacent segmented DC electrodes 725. For example, as illustrated in FIG. 7A, the DC voltage is applied to DC electrodes in blocks of four (e.g., 741, 742, 743 744 and 751, 752, 753 754). The DC voltage is not applied to DC electrodes in blocks of four as well (e.g., 745, 746, 747, 748 and 755, 756, 757, and 758). This forms a square wave, as illustrated in FIG. 7B. As time is stepped forward, the DC transient waveform advances (e.g., from left to right) one DC electrode at a time. That is to say, as time is stepped forward in a first increment, application of the DC voltage to electrode 741 and 751 stops, while application of the DC voltage to electrodes 745 and 755 starts. As time further moves forward, this stepwise progression of the DC transient waveform continues.

(iii) Comparison of Arrival Time Distribution

Figure 8B:
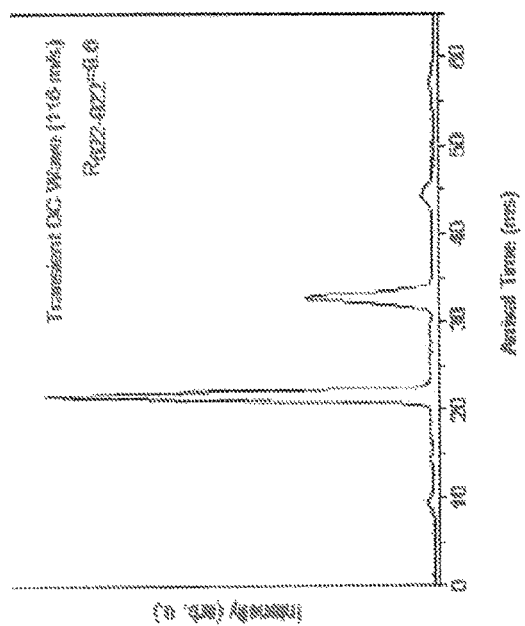
FIG. 8B is a plot of intensity as a function of time illustrating an arrival time distribution for ions possessing a mass to charge ratio (m/z) of 622 and 922 moving through the device of FIG. 7A under the influence of the transient DC voltage waveform of FIG. 8A at speed of 116 m/s.
Figure 8A:
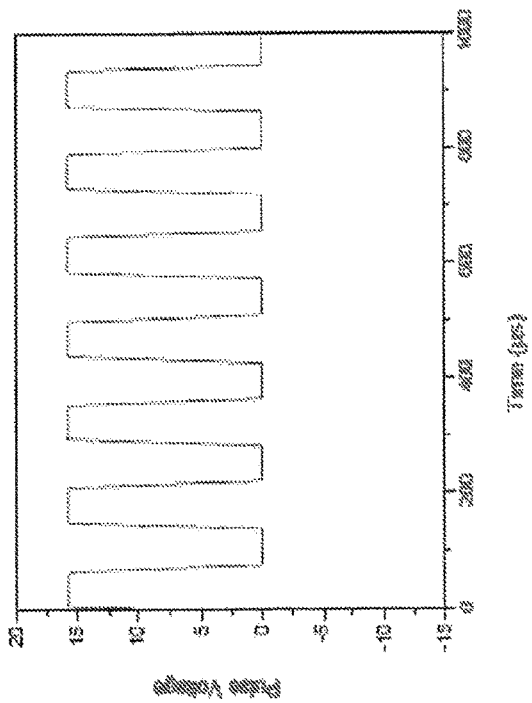
FIG. 8A is a plot of voltage as a function of time illustrating a transient DC voltage waveform with a peak-to-peak amplitude ($V_{p-p}$) of approximately 17V and a frequency of 4 kHz.
Figure 9B:
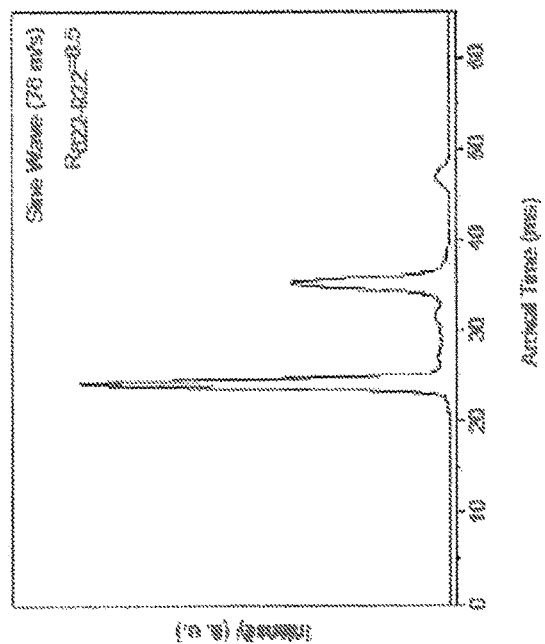
FIG. 9B is a plot of intensity as a function of time illustrating an arrival time distribution for ions possessing a mass to charge ratio (m/z) of 622 and 922 moving through the device of FIG. 1 under the influence of the continuous AC voltage waveform of FIG. 9A at a speed of 76 m/s.
Figure 9A:
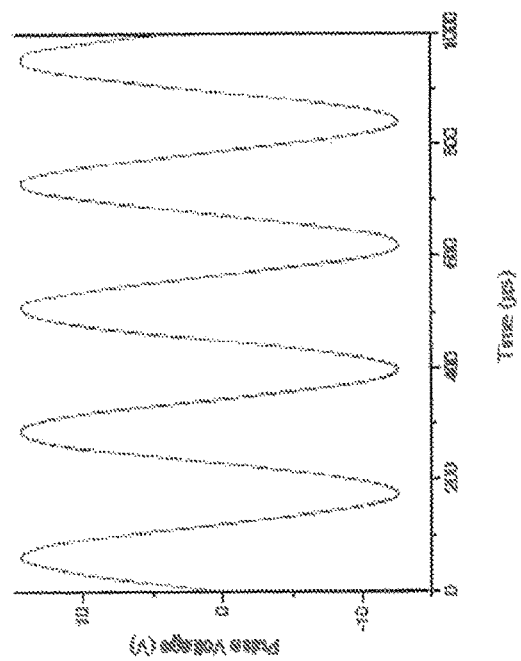
FIG. 9A is a plot of voltage as a function of time illustrating a continuous AC voltage waveform with a peak-to-peak amplitude ($V_{p-p}$) of approximately 35 V and a frequency of 4 kHz.

FIGS. 8A and 9A illustrate the DC transient waveform and the continuous AC waveform, respectively. The applied transient DC wave speed possesses a peak-to-peak amplitude of approximately 17 V and a speed of 116 m/s. The applied continuous AC waveform possesses a peak-to-peak amplitude of approximately 17 $V_{p-p}$ and a sine wave speed of 76 m/s.

FIGS. 8B and 9B illustrate the resultant arrival time distributions using the DC transient waveform and the continuous AC waveform, respectively, on ions having m/z 622-922. Notably, the arrival time measurements of 8B and 9B illustrate that the conventional, transient DC approach and embodiments of the SLIMS-AC approach disclosed herein achieve nearly identical separations.

(iv) Comparison of Resolution

Figure 10:
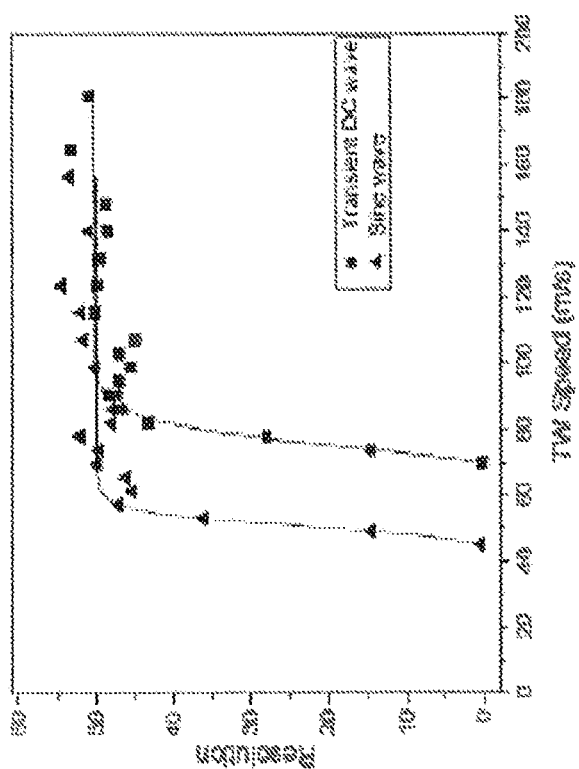
FIG. 10 is a plot of resolution as a function of traveling wave speed illustrating the resolution achieved using the DC voltage waveform of FIG. 7A and the continuous AC voltage waveform of 8A for ions possessing an m/z of 622 and 922 moving through the device of FIGS. 6 and 1, respectively.

FIG. 10 shows the resolutions achieved using the transient DC waveform and the continuous AC waveform generated according to embodiments of the disclosed AC-SLIMS technique, with the m/z 622-922 ions moving through the devices of FIGS. 1 and 7. The traveling wave voltage was 30V, and 5V was applied to the outside guard electrodes. A RF frequency between 628-648 kHz was applied to both PCB surfaces. The amplitude of the RF voltage was 220 V.

Notably, embodiments of the SLIMS AC approach disclosed herein achieve nearly identical resolution as compared to the conventional, transient DC waveform approach.

(iv) Comparison of Electric Field Exposure

Figure 11:
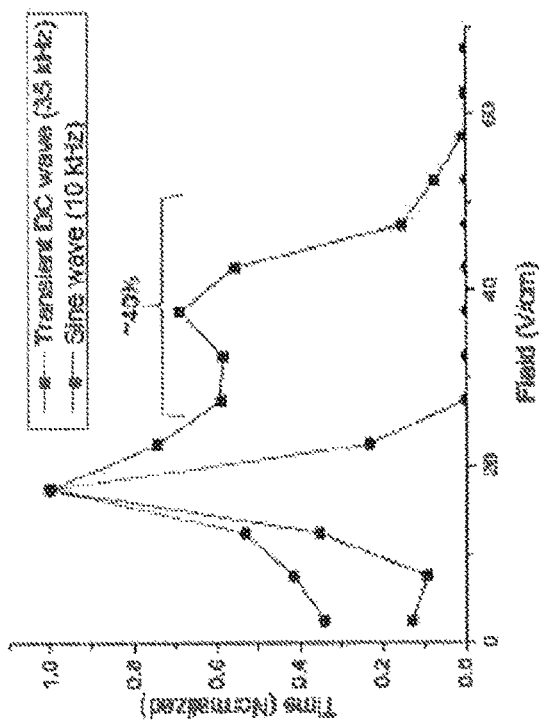
FIG. 11 is a plot of normalized time as a function of electric field strength for ions possessing an m/z of 622-922 moving through the device of FIGS. 6 and 1 using the voltage waveforms of FIGS. 7A and 8A, respectively.

FIG. 11 compares the amount of time the m/z 622-922 ions spend in a high vs. low electric field, using the transient DC waveform and the continuous AC waveform generated according to embodiments of the disclosed AC-SLIMS technique. The frequency of the AC waveform was approximately 10 kHz, and the frequency of the transient DC waveform was approximately 35 kHz. The amplitude of each of the waveforms is 30 V.

The data of FIG. 11 shows that the ions moving under the influence of the transient DC waveform (squares) spent almost 40% of their time in a high electric field, while the ions moving under the influence of embodiments of the disclosed continuous AC waveform (triangles) spent most of their time in a low electric field. From this, it may be concluded that the ions moving under the influence of the continuous AC waveform remain at a lower temperature than the ions moving under the influence of the transient DC waveform. The absence or mitigation of heating is highly beneficial because, as ions are heated, they can undergo dissociation, which is detrimental to the ion separation process.

Example 2—Simulations of Curved Surfaces (i) AC-SLIMS Simulation Parameters

The schematic module shown in FIG. 3 is used for the simulation. The curved AC electrodes 325 are segmented electrodes adjacent to the long, curved RF electrode strips 310, 320. The curved guard electrodes 330 are on the outside of the curved electrodes 310, 320, 325.

The module is fabricated using PCBs and included a single PCB (15 cm long×0.5 cm wide). The module uses 2 sets of AC electrodes 325, separated from adjacent RF electrodes 310 and 320 by 0.3 mm. The dimensions of the AC electrodes 125 are 2 mm in length and 0.4 mm in width. Guard electrodes 130 are each 1 mm wide. The dimensions of the RF electrodes 110 and 120 are each 1 mm in width. The radius of curvature of the electrodes is 3.6 mm.

The module is operated at a pressure of 4 Torr utilizing nitrogen as the buffer gas. Singly charged ions with a mass to charge ratio (m/z) of 622 and 922 were used for the simulations.

RF voltages are applied to the three RF electrodes 310 and 320, 180° out-of-phase for adjacent electrodes to create the pseudopotentials to confine the ions and inhibit ion loss to the PCB. The RF voltage is 300 $V_{p-p}$ in amplitude and 1 MHz in frequency.

DC voltages are applied to the curved guard electrodes to constrain lateral ion motion (in the x-direction). The DC voltage amplitude is 30 V.

An AC voltage waveform is a sinusoid applied over a repeating sequence of eight AC electrodes 325 to move and separate the ions in the longitudinal direction. The applied AC voltage waveform has an amplitude of 30 V and a frequency of 20 KHz. A 45° phase shift of the AC voltage waveform is applied to longitudinally adjacent AC electrodes 325.

(ii) DC-TW Simulation Parameters

FIG. 12 is a top-down view of a module 1200 used for the simulation. The module 1200 includes a curved surface 1205 containing inner DC electrodes 1230 that are laterally offset from outer DC electrodes 1210. RF electrodes 1220 and 1225 are positioned on either side of the inner DC electrodes 1230. The electrodes are coupled to and extend along the length of the surface 1205.

The module is fabricated using a single PCB (15 cm long×0.5 cm wide). The module uses 2 outer DC electrodes 1210, 2 inner DC electrodes 1230, and 2 pairs of RF electrodes 1220, 1225, of opposite phase, RF+ and RF−. Each inner DC electrode 1230 is positioned between an adjacent pair of inner DC electrodes 1220 and 1225. The dimensions of the RF electrodes 1220, 1222 are 76 mm in length and 1 mm in width. Outer DC electrodes 1210 are 2 mm in length and 0.4 mm in width. Inner DC electrodes 1230 are 2 mm in length and 0.4 mm in width. The radius of curvature of the electrodes is 3.5 mm.

The DC voltages applied to the outer DC electrodes 1210 is the same. The voltage applied to inner RF electrodes 1220 is out of phase with its neighboring inner electrode 1225. Fields generated by the potentials applied to the electrodes 1210, 1220, 1225 provide ion confinement. The DC voltage applied to the inner array electrodes 1230 is a time dependent DC field or waveform for moving and separating ions positioned within the module 1200.

The combination of RF and DC fields applied to the electrodes 1210, 1220, 1225, 1230 create, in combination with the shape of the curved surface 1205, confining and driving fields that move ions through the module 1200. Lateral confinement is achievable by a combination of electric fields applied to the outer electrodes 1210 as well as the curvature of the surface 1205. Further details regarding the module 1200 may be found in U.S. patent application Ser. No. 14/851,935, incorporated by reference in its entirety.

The module 1200 is operated at a pressure of 4 Torr utilizing nitrogen as the buffer gas. Singly charged ions with a mass to charge ratio (m/z) of 622 and 922 are used for the simulations.

Figure 13A:
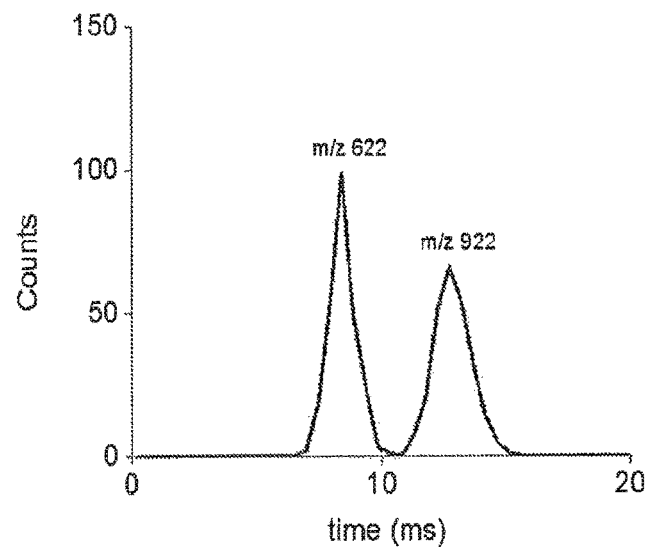
FIG. 13A is a plot of ion counts as a function of time illustrating an arrival time distribution for ions possessing an m/z of 622 and 922 moving through the device of FIG. 12 under the influence of transient DC voltages.
Figure 13B:
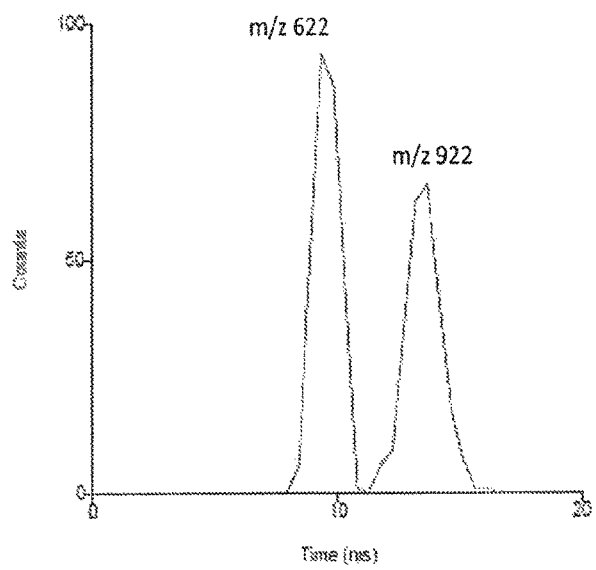
FIG. 13B is a plot of ion counts as a function of time illustrating an arrival time distribution for ions possessing an m/z of 622 and 922 moving through the device of FIG. 3 under the influence of a continuous AC waveform.

FIG. 13A is a plot of ion counts as a function of time illustrating an arrival time distribution for ions possessing a mass to charge ratio (m/z) of 622 and 922 moving through the curved surface device of FIG. 12 under the influence of DC transient voltages. FIG. 13B is a plot of ion counts as a function of time illustrating an arrival time distribution for ions possessing an m/z of 622 and 922 moving through the curved surface device of FIG. 3 under the influence of a continuous AC waveform.

Comparing FIGS. 13A-13B, it is observed that the curved AC-SLIMS module of FIG. 3, employing the continuous AC waveform for ion motion and separation performs comparably to the curved module of FIG. 12, employing the DC transient voltages.

While a number of embodiments of the present disclosure have been shown and described, it will be apparent to those skilled in the art that many changes and modifications may be made without departing from the disclosure in its broader aspects. The appended claims, therefore, are intended to cover all such changes and modifications as they fall within the true spirit and scope of the disclosure.

We claim:

1. An apparatus for ion manipulations, comprising:
   at least one surface;
   a first plurality of continuous electrodes coupled to the at least one surface and in electrical communication with a radiofrequency (RF) voltage source, wherein an RF voltage applied to adjacent electrodes of the first plurality of electrodes by the RF voltage source is phase shifted on the adjacent electrodes of the first plurality of electrodes by substantially 180°; and
   a second plurality of segmented electrodes coupled to the at least one surface and arranged in longitudinal sets of electrodes which are distributed along the longitudinal axis of the surface of the apparatus for ion manipulations between the first plurality of electrodes, the second plurality of segmented electrodes being further in electrical communication with an alternating current (AC) voltage source, wherein an AC voltage waveform applied to adjacent electrodes within a longitudinal set of the second plurality of segmented electrodes by the AC voltage source is phase shifted on the adjacent electrodes of the second plurality of electrodes by 1°-359°.

2. The apparatus of claim 1, further comprising a plurality of guard electrodes positioned on outer ends of the first and second plurality of electrodes on the at least one surface, the plurality of guard electrodes being further in electrical communication with a DC voltage source, wherein the plurality of guard electrodes generate electric fields that constrain ion motion towards the guard electrodes when receiving a constant DC voltage from the DC voltage source.

3. The apparatus of claim 1, wherein the AC voltage waveform is a sine wave.

4. The apparatus of claim 3, wherein the AC voltage waveform is the sum of more than one AC voltage waveform.

5. The apparatus of claim 1, wherein the AC voltage waveform applied to adjacent electrodes within a longitudinal set of the second plurality of segmented electrodes is phase shifted on the adjacent electrodes of the second plurality of segmented electrodes in a repeating pattern.

6. The apparatus of claim 5, wherein the AC voltage waveform applied to adjacent electrodes within a longitudinal set of the second plurality of segmented electrodes is phase shifted by substantially 45°, 90° or 120° on the adjacent electrodes of the second plurality of electrodes in a stepwise fashion.

7. The apparatus of claim 1, wherein the at least one surface comprises a single and non-planar surface.

8. The apparatus of claim 7, wherein the single, non-planar surface is one of the following shapes: curved, cylindrical, a spiral, a funnel, hemispherical, or elliptical.

9. The apparatus of claim 1, wherein the at least one surface comprises two surfaces spaced apart from one another.

10. The apparatus of claim 9, wherein the two surfaces are substantially parallel to one another.

11. The apparatus of claim 1, wherein a frequency of the applied AC voltage waveform is selected from the range of 10 Hz-200 kHz, and a frequency of the applied RF voltage is selected from the range of 100 kHz-5 MHz.

12. The apparatus of claim 1, wherein a frequency applied AC voltage waveform is selected from the range of 1 Hz to 1 kHz.

13. The apparatus of claim 1, wherein a pressure range of the apparatus is from atmospheric pressure to 1 mtorr vacuum.

14. A method for performing ion manipulations, comprising:
   providing at least one surface comprising:
   a first plurality of continuous electrodes coupled to the at least one surface and in electrical communication with a radiofrequency (RF) voltage source; and
   a second plurality of segmented electrodes coupled to the at least one surface and arranged in longitudinal sets of electrodes which are distributed along the longitudinal axis of the surface of the apparatus for ion manipulation between the first plurality of electrodes, the second plurality of segmented electrodes being further in electrical communication with an alternating current (AC) voltage source;
   applying, by the RF voltage source, an RF voltage to adjacent electrodes of the first plurality of electrodes, wherein the applied RF voltage is phase shifted on the adjacent electrodes of the first plurality of electrodes by substantially 180°; and
   applying, by the AC voltage source, an AC voltage waveform within a longitudinal set of the second plurality of segmented electrodes, wherein the applied AC voltage waveform is phase shifted on the adjacent electrodes of the second plurality of electrodes by 1°-359°.

15. The method of claim 14, further comprising positioning a plurality of guard electrodes on outer ends of the first and second plurality of electrodes on the at least one surface, the plurality of guard electrodes being further in electrical communication with a DC voltage source, wherein the plurality of guard electrodes generate electric fields that constrain ion motion towards the guard electrodes when receiving a constant DC voltage from the DC voltage source.

16. The method of claim 14, wherein the AC voltage waveform is a sine wave.

17. The method of claim 16, wherein the AC voltage waveform is the sum of more than one AC voltage waveform.

18. The method of claim 14, wherein the applied AC voltage waveform is phase shifted on the adjacent electrodes of the second plurality of segmented electrodes in a repeating pattern.

19. The method of claim 18, wherein the applied AC voltage waveform is phase shifted by substantially 45°, 90°, or 120°, on the adjacent electrodes of the second plurality of segmented electrodes in a stepwise fashion.

20. The method of claim 14, wherein the at least one surface comprises a single and non-planar surface.

21. The method of claim 20, wherein the single, non-planar surface is one of the following shapes: curved, cylindrical, a spiral, a funnel, hemispherical, or elliptical.

22. The method of claim 14, wherein the at least one surface comprises two surfaces spaced apart from one another.

23. The method of claim 22, wherein the two surfaces are substantially parallel to one another.

24. The method of claim 14, wherein a frequency of the applied AC voltage waveform is selected from the range of 10 Hz-200 kHz, and a frequency of the RF voltage is selected from the range of 100 kHz-5 MHz.

* * * * *